US008329400B2

(12) United States Patent
Lok

(10) Patent No.: US 8,329,400 B2
(45) Date of Patent: *Dec. 11, 2012

(54) METHODS FOR NUCLEIC ACID MAPPING AND IDENTIFICATION OF FINE-STRUCTURAL-VARIATIONS IN NUCLEIC ACIDS

(75) Inventor: Si Lok, Honk Kong (CN)

(73) Assignee: Versitech Limited, Hong Kong (CN)

( * ) Notice: Subject to any disclaimer, the term of this patent is extended or adjusted under 35 U.S.C. 154(b) by 353 days.

This patent is subject to a terminal disclaimer.

(21) Appl. No.: 12/501,136

(22) Filed: Jul. 10, 2009

(65) Prior Publication Data
US 2009/0325239 A1 Dec. 31, 2009

Related U.S. Application Data

(63) Continuation-in-part of application No. 11/954,947, filed on Dec. 12, 2007, now abandoned, which is a continuation-in-part of application No. 11/649,587, filed on Jan. 3, 2007, now Pat. No. 7,932,029.

(60) Provisional application No. 61/129,660, filed on Jul. 10, 2008, provisional application No. 61/193,442, filed on Dec. 1, 2008, provisional application No. 60/756,417, filed on Jan. 4, 2006, provisional application No. 60/792,926, filed on Apr. 17, 2006, provisional application No. 60/814,378, filed on Jun. 15, 2006.

(51) Int. Cl.
*C12Q 1/68* (2006.01)
(52) U.S. Cl. ........ 435/6.1; 536/22.1; 536/23.1; 536/24.3
(58) Field of Classification Search ........... 435/6, 320.1, 435/6.1; 536/22.1, 23.1, 24.1
See application file for complete search history.

(56) References Cited

U.S. PATENT DOCUMENTS

| | | | | |
|---|---|---|---|---|
| 5,459,072 A | * | 10/1995 | McKay et al. | 435/320.1 |
| 5,695,937 A | | 12/1997 | Kinzler et al. | |
| 5,830,645 A | | 11/1998 | Pinkel | |
| 5,843,654 A | * | 12/1998 | Heisler et al. | 435/6 |
| 5,874,259 A | | 2/1999 | Szybalski | |
| 6,100,035 A | * | 8/2000 | Kauffman et al. | 435/6 |
| 6,159,685 A | | 12/2000 | Pinkel et al. | |
| 6,709,861 B2 | | 3/2004 | Mead et al. | |
| 6,720,179 B1 | * | 4/2004 | Macevicz | 435/320.1 |
| 6,730,500 B1 | | 5/2004 | Lok | |
| 7,932,029 B1 | * | 4/2011 | Lok | 435/6.12 |
| 2001/0005749 A1 | * | 6/2001 | Cahoon et al. | 536/23.2 |
| 2003/0224380 A1 | * | 12/2003 | Becker et al. | 435/6 |
| 2005/0123947 A1 | * | 6/2005 | Quake et al. | 435/6 |
| 2005/0233364 A1 | * | 10/2005 | Burgess et al. | 435/6 |
| 2006/0166252 A1 | * | 7/2006 | Ladner et al. | 435/6 |
| 2006/0292611 A1 | | 12/2006 | Berka et al. | |

OTHER PUBLICATIONS

Cohen et al., PNAS 70(11) : 3240 (1973).*
Matthews et al., Analytical Biochemistry 169 : 1 (1988).*
TA Cloning Kit Manual from Invitrogen Version V , 31 pages, (Apr. 2004).*
Albertson, D.G. and Pinkel, D., 2003. Genomic microarrays in human genetic disease and cancer. *Human Molecular Genetics*, 12 Spec No. 2: R145-R152.
Albertson, D.G,, et al., 2000. Quantitative mapping of amplicon structure by array CGH identifies *CYP24* as a candidate oncogene. *Nature Genetics 25*: 144-146.
Andersson, L., 2001. Genetic Dissection of Phenotypic Diversity in Farm Animals. *Nature Reviews 2*: 130-138.
Bailey, A.B., et al., 2002. Recent Segmental Duplications in the Human Genome. *Science 297*: 1003-1007.
Batzoglou, S., et al., 2002. Arachne: A Whole-Genome Shotgun Assembler. *Genome Research 12*: 177-189.
Bignell, G.R. et al., 2004. High-Resolution Analysis of DNA Copy Number Using Oligonucleotide Microarrays. *Genome Research 14*: 287-295.
Bolivar, F. et al., 1977. Construction and Characterization of New Cloning Vehicles. II A Multipurpose System. *Gene 2*: 95-113.
Brennan, C., et al., 2004. High-Resolution Global Profiling of Genomic Alterations with Long Oligonucleotide Microarray. *Cancer Research 64*: 4744-4748.
Bujnicki, J.M., 2001. Understanding the evolution of restriction-modification systems: Clues from sequence and structure comparisons. *Acta Biochimica Polonica* vol. 48 No. 4: 935-967.
Buryanov, Y.I., et al., 1978. Site Specific and Chromatographics Properties of *E coli* K12 and *Eco*RII DNA-Cytosine Methylases. *FEBS Letters 88*: 251-254.
Chang, A.C.Y. and Cohen, S.N., 1978. Construction and Characterization of Amplifiable Multicopy DNA Cloning Vehicles Derived from the P15A Cryptic Miniplasmid. *Journal of Bacteriology*, vol. 134, No. 3: 1141-1156.
Check, E., 2005. Patchwork people. *Nature 437*: 1084-1096.
Cheng, Z., et al., 2005. A genome-wide comparison of recent chimpanzee and human segmental duplications. *Nature 437*: 88-93.

(Continued)

*Primary Examiner* — Ethan C Whisenant
(74) *Attorney, Agent, or Firm* — Saliwanchik, Lloyd & Eisenschenk

(57) ABSTRACT

A method of juxtaposing sequence tags (GVTs) that are unique positional markers along the length of a population of target nucleic acid molecules is provided, the method comprising: fragmenting the target nucleic acid molecule to form target DNA insert; ligating the target DNA insert to a DNA vector or backbone to create a circular molecule; digesting the target DNA insert endonuclease to cleave the target DNA insert at a distance from each end of the target DNA insert yielding two GVTs comprising terminal sequences of the target DNA insert attached to an undigested linear backbone; recircularizing the linear backbone with the attached GVTs to obtain a circular DNA containing a GVT-pair having two juxtaposed GVTs; and recovering the GVT-pair DNA by nucleic acid amplification or digestion with endonuclease having sites flanking the GVT-pair. Cosmid vectors are provided for creating GVT-pairs of ~45- to 50-kb separation sequencable by next-generation DNA sequencers.

42 Claims, No Drawings

OTHER PUBLICATIONS

Collins, F.S., et al., 1987. Construction of a General Human Chromosome-Jumping Library, with Application in Cystic Fibrosis. *Science 235*: 1046-1049.

Collins, F.S., and Weissman, S.M., 1984. Directional cloning of DNA fragments at a large distance from an initial probe: A circularization method. *Proc. Natl. Acad. Sci. (USA)* 81: 6812-6816.

Craddock, N. and Jones, I., 2001. Molecular genetics of bipolar disorder. *British Journal of Psychiatry 178, Suppl 41*: S128-S133.

Deininger, P.L., 1983. Random Subcloning of Sonicated DNA: Application to Shotgun DNA Sequence Analysis. *Analytical Biochemistry 129*: 216-223.

Dugaiczyk, A. et al., 1975. Ligation of *Eco* RI Endonuclease-generated DNA Fragments into Linear and Circular Structures. *J Mol Biol 96*: 171-178.

Dunn, J.L., et al., 2002. Genomic Signature Tags (GSTs): A System for Profiling Genomics DNA. *Genome Research 12*: 1756-1765.

Edwards, A., et al., 1990. Automated DNA Sequencing of the Human *HPRT* Locus. *Genomics 6*: 593-608.

Feng, T., et al., 2002. Increased Efficiency of Cloning Large DNA Fragments Using a Lower Copy Number Plasmid. *BioTechniques 32*: 992-998.

Feuk, L., et al., 2006. Structural variation in the human genome. *Nature Reviews 7*: 85-97.

Fitzgerald, M.C., et al., 1992. Rapid shotgun cloning utilizing the two base recognition endonuclease *Cvi*JI. *Nucleic Acids Research* vol. 20, No. 14: 3753-3762.

Geier, G.E. and Modrich, P., 1979. Recognition Sequence of the *dam* Methylase of *Escherichia coli* K12 and Mode of Cleavage of *Dpn* I Endonuclease. *Journal of Biological Chemistry 254*: 1408-1413.

Gonzalez, E., et al., 2005. The influence of *CCL3L1* Gene-Containing Segmental Duplications on HIV-1/AIDS Susceptibility. *Science 307*: 1434-1440.

Gray, J.W. and Collins, C., 2000. Genome changes and gene expression in human solid tumors. *Carcinogenesis 21*: 443-452.

Grindley, N.D.F. and Joyce, C.M., 1980. Genetic and DNA sequence analysis of the kanamycin resistance transposon Tn*903*. *Proc. Natl. Acad. Sci. (USA)* 77: 7176-7180.

Hamelin, C. and Yelle, J., 1990. Gel and buffer effects on the migration of DNA molecules in agarose. *Applied Theoretical Electrophoresis 1*: 225-231.

Hattman, S., et al., 1978. Sequence Specificity of the P1 Modification Methylase (M.*Eco* P1) and the DNA Methylase (M.*Eco* dam) Controlled by the *Escherichia coli* dam gene. *J Mol Biol 126*: 367-380.

Havlak, P., et al., 2004. The Atlas Genome Assembly System. *Genome Research 14*: 721-732.

Hayashi, K., et al., 1986. Regulation of inter- and intermolecular ligation with T4 DNA ligase in the presence of polyethylene glycol. *Nucleic Acids Research 14*: 7617-7630.

Heffron, F., et al., 1978. In vitro mutagenesis of a circular DNA molecule by using synthetic restriction sites. *Proc Natl Aced Sci (USA)* 74: 6012-6016.

Heiskanen, M.A., et al., 2000. Detection of Gene Amplification by Genomic Hybridization to cDNA Microarrays. *Cancer Research 60*: 799-802.

Holzman, P.S., and Matthysse, S., 1990. The Genetics of Schizophrenia: A Review. *Psychological Science 1*: 179-286.

Huang, J., et al., 2004. Whole genome DNA copy number changes by high density oligonucleotides arrays. *Human Genomics 1*: 287-299.

Huang, X., et al., 2006. Application of a superword array in genome assembly. *Nucleic Acids Research 34*: 201-205.

Huang, X., et al., 2003. PCAP: A Whole-Genome Assembly Program. *Genome Research 13*: 2164-2170.

Inazawa, J., et al., 2004. Comparative genomic hybridization (CGH)-arrays pave the way for identification of novel cancer-related genes. *Cancer Sci 95*: 559-563.

Jaffe, D.B., et al., 2003. Whole-Genome Sequence Assembly for Mammalian Genomes: Arachne 2. *Genome Research 13*: 91-96.

Kan, N.C., et al., 1979. The Nucleotide Sequence Recognized by the *Escherichia coli* K12 Restriction and Modification Enzymes. *J Mol Biol 130*: 191-209.

Korbel, J.O., et al., 2007. Paired-End Mapping Reveals Extensive Structure Variation in the Human Genome. *Science 318*: 420-426.

Kozdroj, J. and Van Elsas, J.D., 2001. Structural diversity of microorganisms in chemically perturbed soil assessed by molecular and cytochemical approaches. *Journal of Microbiological Methods 43*: 187-212.

Lucito, R. et al., 2003. Representational Oligonucleotide Microarray Analysis: A High-Resolution Method to Detect Genome Copy Number Variation. *Genome Research 13*: 2291-2305.

Mackay, T.F.C., 2001. Quantitative Trait Loci in *Drosophila*. *Nature Reviews, Genetics 2*: 11-20.

Mahairas, G.G., et al., 1999. Sequence-tagged connectors: A sequence approach to mapping and scanning the human genome. *Proc Natl Acad Sci (USA)* 96: 9739-9744.

Mardis, E.R., 2008. Next-Generation DNA Sequencing Methods. *Annu Rev Genomics Hum Genet 9*: 387-402.

Margulies, M., et al., 2005. Genome sequencing in microfabricated high-density picolitre reactors. *Nature 437*: 376-380.

Matsumura, H., et al., 2003. Gene expression analysis of plant host-pathogen interactions by SuperSAGE. *Proc Natl Acad Sci (USA)* 100: 15718-15723.

May, M.A. and Hattman, S., 1975. Analysis of Bacteriophage Deoxyribonucleic Acid Sequences Methylated by Host- and R-Factor-Controlled Enzymes. *Journal of Bacteriology 123*: 768-770.

McClelland, M. et al., 1994. Effect of site-specific modification on restriction endonucleases and DNA modification methyltransferases. *Nucleic Acids Research 22*: 3640-3659.

Melgar, E. and Goldthwait, D.A., 1968. Deoxyribonudeic Acid Nucleases: II. The Effect of Metals on the Mechanism of Action of Deoxyribonuclease I. *Journal of Biological Chemistry 243*: 4409-4416.

Morozova, O., and Marra, M.A., 2008. Applications of the next-generation sequencing technologies in functional genomics. *Genomics 92*: 255-262.

Mullikin, J.C. and Ning, Z., 2003. The Phusion Assembler. *Genome Research 13*: 81-90.

Myers, E.W., et al., 2000. A Whole-Genome Assembly of *Drosophila*. *Science 287*: 2196-21204.

Ng, P., et al., 2005. Gene identification signature (GIS) analysis for transcriptome characterization and genome annotation. *Nature Methods 2*: 105-111.

Owen, M.J. and Craddock, N., 1996. Modern molecular genetic approaches to complex traits: Implications for psychiatric disorders. *Molecular Psychiatry 1*: 21-26.

Pevzner, P.A. and Tang, H., 2001. Fragment assembly with double-barreled data. *Bioinformatics 17 Suppl 1*: S225-S233.

Pheiffer, B.H. and Zimmerman, S.B., 1983. Polymer-stimulated ligation: enhanced blunt- or cohesive-end ligation of DNA or deoxyribooligonucleotides by T4 DNA ligase in polymer solutions. *Nucleic Acids Research 11*: 7853-7871.

Pinkel, D. and Albertson, D.G., 2005. Array comparative genomic hybridization and its application in cancer. *Nature Genetics Suppl 37*: S11-S17.

Pinkel, D., et al., 1998. High resolution analysis of DNA copy number variation using comparative genomic hybridization to microarrays. *Nature Genetics 20*: 207-211.

Pollack, J.R., et al., 2002. Microarray analysis reveals a major direct role of DNA copy number alternation in the transcriptional program of human breast tumors. *Proc Natl Acad Sci (USA)* 99: 12963-12968.

Pollack, J.R., et al., 1999. Genome-wide analysis of DNA copy-number changes using cDNA microarrays. *Nature Genetics 23*: 41-46.

Pop, M. et al., 2004. Comparative genome assembly. *Briefings in Bioinformatics 5*: 237-248.

Redon, R., et al., 2006. Global variation in copy number in the human genome. *Nature 444*: 444-454.

Rouillard, J-M., et al., 2001. Virtual Genome Scan: A Tool for Restriction Landmark-Based Scanning of the Human Genome. *Genome Research 11*: 1453-1459.

Saha, S., et al., 2002. Using the transcriptome to annotate the genome. *Nature Biotechnology 19*: 508-512.

Salzberg, S.L., and Yorke, J.A., 2005. Beware of mis-assembled genomes. *Bioinformatics 21*: 4320-4321.

Sanger, F. et al., 1977. DNA sequencing with chain terminating inhibitors. *Proc Natl Acad Sci (USA)* 74: 5463-5467.

Schloter, M., et al., 2000. Ecology and evolution of bacterial microdiversity. *FEMS Micobiology Reviews 21*: 647-660.

Schriefer, L.A., et al., 1990. Low pressure DNA shearing: A method for random DNA sequence analysis. *Nucleic Acids Research 18*: 7455.

Sistla, S. and Rao, D.N., 2004. S-Adenosyl-L-Methionine-Dependent Restriction Enzymes. *Critical Reviews in Biochemistry and Molecular Biology 39*:1-19.

Snijders, A.M. et al., 2001. Assembly of microarrays for genome-wide measurement of DNA copy numbers. *Nature Genetics 29*: 263-264.

Szybalski, E., et al., 1991. Class-IIS restriction enzymes—a review. *Gene 100*: 13-26.

Tao, Q. and Zhang, H-B, 1998. Cloning and stable maintenance of DNA fragments over 300 kb in *Escherichia coli* with conventional plasmid-based vectors. *Nucleic Acids Research 21*: 4901-4909.

Tuzun, E., et al., 2005. Fine-scale structural variation of the human genome. *Nature Genetics 37*: 727-732.

Velculescu, V.E., et al., 1995. Serial Analysis of Gene Expression. *Science 270*: 484-487.

Volik, S., et al., 2006. Decoding the fine-scale structure of a breast cancer genome and transcriptome. *Genome Res 16*: 394-404.

Wang, J.C. and Davidson, N., 1966. On the probability of ring closure of lambda DNA. *J Mol Biol 19*: 469-482.

Warren, R.L., et al., 2006. Physical map-assisted whole-genome shotgun sequence assemblies. *Genome Res 16*: 768-775.

Wei, C-L. et al., 2004. 5' long serial analysis of gene expression (LongSAGE) and 3' LongSAGE for transcriptome characterization and genome annotation. *Proc Natl Acad Sci (USA)* 101: 11701-11706.

Weinstock, G.M., et al., 2006. Insights into social insects from the genome of the honeybee *Apis mellifera*. *Nature 443*: 931-949.

Wimmer, K., et al., 2002. Combined restriction landmark genomic scanning and virtual genome scans identify a novel human homeobox gene, *ALX3*, that is hypermethylated in neuroblastoma. *Genes Chromosomes & Cancer 33*: 285-294.

Zhang, Z., et al., 2000. A greedy algorithm for aligning DNA sequencing. *J Computational Biol 7*: 203-214.

Zhao, S., 2000. Human BAC ends. *Nuc Acids Res 28*: 129-132.

Zimmerman, S.B. and Pheiffer, B.H., 1983. Macromolecular crowding allows blunt-end ligation by DNA ligases from rat liver or *Escherichia coli*. *Proc Natl Acad Sci (USA)* 80: 5852-5856.

\* cited by examiner

METHODS FOR NUCLEIC ACID MAPPING AND IDENTIFICATION OF FINE-STRUCTURAL-VARIATIONS IN NUCLEIC ACIDS

CROSS-REFERENCE TO RELATED APPLICATIONS

This application claims the benefit of Provisional Application Ser. No. 61/129,660, filed Jul. 10, 2008, and Provisional Application Ser. No. 61/193,442, filed Dec. 1, 2008. This application is also a Continuation-In-Part of Serial No. 11/954,947, filed Dec. 12, 2007 now abandoned, which is a Continuation-In-Part of Ser. No. 11/649,587, filed Jan. 3, 2007 now U.S. Pat. No. 7,932,029, which claims the benefit of Provisional Application Ser. Nos. 60/756,417, filed Jan. 4, 2006; 60/792,926, filed Apr. 17, 2006; and Ser. No. 60/814,378, filed Jun. 15, 2006.

FIELD OF THE INVENTION

The present invention relates generally to methods for high-throughput analysis of fine structural variations in nucleic acids. In particular, the present invention relates to novel strategies, vectors and other components to produce pairs of linked-nucleic acid tags, wherein constituent members of a linked nucleic acid tag-pair are of a user defined separation distance, and/or are markers of nucleic acid positions that demarcate adjacent cleavage sites for one or more different restriction endonucleases along the length of a target nucleic acid molecule. In a preferred embodiment, the present invention is used to identify genomic alterations or markers that could be correlated to a phenotype. In another preferred embodiment, the present invention is used to create high-resolution genomic maps to aid genomic assembly from shotgun DNA sequencing.

BACKGROUND OF THE INVENTION

While the most abundant type of variant in the human genome and the best-studied is the single-nucleotide polymorphism (SNP), it is increasingly clear that the so termed "fine-structural-variations" comprising alterations of copy number (insertions, deletions and duplications), inversions, translocations and other sequence rearrangements are integral features of the human and other genomes. These types of variations appear to be present in much greater frequency in the general population than originally thought. Evidence is mounting to indicate that structural variants can comprise millions of nucleotides of heterogeneity in each individual. Understanding the role of fine-structural-variations in genome evolution, interaction with the environment, phenotypic diversity and in disease are among the most actively investigated areas of current genomic research. For review, refer to Feuk et al (2006), Redon et al (2006), Check (2005), Cheng et al (2005), and Bailey et al (2002).

In comparison to analysis of SNPs, efficient high throughput methods for analysis of fine-structural-variations are not well developed. An important first step is the technique of array comparative genomic hybridization (array CGH) (Pinkel et al, 1998; Pinkel et al, U.S. Pat. Nos. 5,830,645 and 6,159,685), which enables the qualification of relative copy numbers between a target DNA and a reference DNA. Array CGH allows reliable detection of deoxyribonucleic acid (DNA) copy-number differences between DNA samples with a resolution at the level of a single arrayed bacterial artificial chromosome (BAC) clone (Snijders et al, 2001; Albertson et al, 2000; Pinkel et al, 1998). The adaptation of array CGH to cDNA (Heiskanen et al, 2000; Pollack et al, 1999) and to high-density oligo-nucleotide array platforms (Bignell et al, 2004; Brennan et al, 2004; Huang et al, 2004; Lucito et al, 2003) further extends the resolution and utility of this approach. Through its use, array CGH has led to the identification of gene copy number alterations that are associated with tumor (Pinkel and Albertson, 2005; Inazawa et al, 2004; Albertson and Pinkel, 2003; Pollack et al, 2002) and disease progression (Gonzalez et al, 2005).

1. Fosmid Pair-End Mapping

Despite the usefulness for copy number determination, array CGH is not suited to address other types of genomic structural variations, most notably, inversions, translocations and other types of nucleic acid rearrangements. Tuzun et al (2005) attempt to address these limitations with an approach termed "fosmid paired-end mapping." This approach relies on the head-full mechanism of fosmid packaging to produce genomic DNA libraries with reasonably uniform ~40-kilobase pairs (kb) size genomic inserts from test subjects. Experimentally, the actual fragments range from 32- to 48-kb, <3 standard deviations from the mean, 39.9+/−2.76-kb. End-terminal sequencing of the randomly selected ~40-kb library inserts produces pairs of short sequence tags in which each tag-pair marks two genomic positions with separation of approximately 40-kb along the lengths of the target DNA. The tag-pairs are then computationally aligned to a reference genomic assembly and any discordance with either their expected orientation or with their ~40-kb separation distance, would denote the presence of at least one structural difference between the target and the reference nucleic acid spanning that region. Tag-pairs having map positions that are separated by more than 40-kb signify the presence of a deletion on the target DNA in respect to the reference; map positions with separation of less than 40-kb signify an insertion of DNA in the target. Inconsistencies in the orientation of the pair of mapped tags denote potential DNA inversions or other complex chromosomal rearrangements. Chromosomal translocations are signified by assignment of the tag-pair to two different chromosomes on the reference sequence. Analysis of over a million individually purified fosmid clone inserts by conventional DNA sequencing enabled Tuzun et al (2005) to identify nearly 300 sites of structural variations between test subject and the reference genomic assembly.

The authors did not teach or disclose other methods to create tag-pairs, to create tag-pairs of different spacing to change the spatial resolution of analysis, to improve the homogeneity of the insert lengths in their library, to improve economy by use of the generation DNA sequencers, nor disclose methods to produce other types of sequence tag-pairs such as those of the present invention that can demarcate genomic positions based on the location and/or separation distance between pairs of adjacent endonuclease cleavage sites.

Many types of fine-structural-variations are not resolved by the ~40-kb resolution window fixed by the fosmid-paired end mapping approach. Fosmid paired-end mapping has further limitations. Fosmid vectors propagate in host cells at a very low copy number, a property used to minimize potential recombination, rearrangement and other artifacts encountered during the propagation of certain genomic sequences in a microbial host. Despite the current use of amplifiable versions of fosmid vectors (Szybalski, U.S. Pat. No. 5,874,259) terminal sequencing of fosmid clones to generate sequence tags still has very poor economy due to low DNA yield when compared to conventional plasmids, making high-throughput automated template production and sequencing difficult to maintain. Furthermore, two separate sequence reactions are required to generate a tag-pair sequence from a single fosmid DNA template, thereby reducing the economy further.

While fosmid paired-end mapping is a useful start to identify fine-structural-variations in the human genome, immense cost and logistical efforts required to purify and sequence more than a million fosmid insert ends for each test subject preclude its use in broad population and cohort surveys to identify genomic variations that could be associated with complex diseases or in response to environmental factors and the like. Moreover, fosmid vectors and their variants generally propagate in very low copy-numbers in host cells making reliable automated DNA production and sequencing difficult to maintain. Hence, there is a need for an efficient, robust high throughput and low cost method for the identification of fine-structural-variations for use in genomic and association studies to link these genetic elements to disease, disease progression and disease susceptibility.

2. Existing Methods for the Generation of Genomic Tags

A variety of DNA-based fingerprinting approaches have been described in the art to characterize and to compare genomes (Wimmer et al, 2002; Kozdroj and van Elsas, 2001; Rouillard et al, 2001; Schloter et al, 2000). All these approaches employed some combinations of restriction endonuclease digestion of target DNA, PCR amplification, or gel electrophoretic separation. In common, these approaches are laboriously encumbered by the need to extract candidate DNA fragments from gels for DNA sequencing. A step forward was the work of Dunn et al (2002) where they described a method using the type IIS/type IIG restriction endonuclease, Mme I, to generate "Genomic Signature Tags" (GSTs) for analyzing genomic DNA. GSTs were generated by ligation of adaptors bearing a Mme I recognition site to genomic DNA fragments that were initially created by an initial digestion of the target genomic DNA with a type II restriction endonuclease followed by a second digestion with a frequent cutting tagging enzyme. Digestion of the adaptor ligated DNA with Mme I created a 21-bp tag (GST) with a fixed position in the DNA relative to the sites recognized by the initial restriction enzyme digestions. Following amplification by PCR, purified GSTs were oligomerized for cloning and DNA sequencing. The identity of the tags and their relative abundance were used to create a high-resolution "GST sequence profile" of genomic DNA that can be used to identify and quantify the genome of origin within a given complex DNA isolate. Using *Yersinia pestis* as a model system, Dunn et al (2002) were able to define regions in a relatively simple genome that might have undergone changes that added or deleted restriction sites. However, the method of Dunn et al (2002) has limited utility for complex genomes such as man, where most structural variations are not revealed by the simple gain or lost of a site for a small number of restriction endonucleases under investigation. Moreover the number of GSTs required to cover a large genome or to analyze multiple samples for even one restriction site is prohibitive. In contrast, the GVT-pairs of the present invention provide the economy and the analytical power to profile complex genomes or to extend analysis to multiple DNA samples.

Versions of a method known as Serial Analysis of Gene Expression (SAGE), first described by Velculescu et al (1995) and Kinzler et al (1995) (U.S. Pat. No. 5,695,937), also made use of a type ITS or a type IIG restriction endonuclease to generate DNA tags (Ng et al, 2005; Wei et al, 2004; Saha et al, 2002). The so termed "SAGE tags" were generated from cDNA templates to provide an assessment of the complexity and relative abundance of cDNA species in a biological sample. Later versions of SAGE referred to as "LongSAGE" made use of Mme I digestion to create sequence tags of 21-bp to tag mRNA transcripts (Saha et al, 2002). The most current refinement termed "SuperSAGE" made use of the type III restriction endonuclease, EcoP15 I, to produce a longer tag of 25- to 27-bp for improved mRNA assignment to the genome (Matsumura et al, 2003). Although the present invention also makes use of type IIS, type IIG or type III restriction endonucleases to generate sequence tags, the resulting GVT-pairs of the invention are fundamentally different from the aforementioned SAGE and GST tags by methods of production as well as by improved informational content. Pairs of spatial linked tags of the present invention offer a marked improvement in efficiency and analytical power over the use of a single unlinked tag for generation of high-resolution physical maps that are particularly useful for characterizing novel genomes or for annotating genomes and DNA samples for fine-structural-variations.

The recent work of Ng et al (2005) described a further development of the SAGE method. The investigators made use of a method pioneered by Collins and Weissman (1984) where circularization of a DNA fragment, also referred to as intra-molecular DNA ligation, was employed to link distal DNA segments together into a vector to produce the so termed "genomic jumping libraries" (Collins et al, 1987). Ng et al circularized individual cDNAs to link their 5'- and 3'-derived SAGE tags together to produce "Paired-End Ditags" (PETs), which are then oligomerized to facilitate efficient sequencing. PETs are useful for genomic annotation by the identification of transcription start sites and poly-adenylation sites of transcription units to demarcate gene boundaries and to aid the identification of their flanking regulatory sequences. While the GVT-pair of the present invention and PET both rely on intra-molecular ligation to achieve linkage of DNA markers, only the GVT-pair of the present invention integrates physical distance and other useful information, such as linkage of adjacent restriction sites, thereby making the GVT-pair unique and useful for detailed genomic structural analysis. Ng et al (2005) did not teach methods to create spatially defined tags or tags based on other criteria as described in the present disclosure, neither did they reveal how genomic fine-structural-variations can be derived using their PET approach, nor other methods to generate sequence tag other than through the exclusive use of the type ITS restriction endonuclease Mme I. Finally, Ng et al (2005) did not anticipate methods to enable the efficient use of the next generation of short read DNA sequencers.

Berka et al (2006) (U.S. Patent Application 2006/0292611) and Kobel et al (2007) recently described a method of pair-end mapping of DNA that is functionally similar to the present invention, but their method differs fundamentally in the spatial orientation of the final tagged DNA product and suffers certain important disadvantages. In the method of Kobel et al (2007) and Berka et al (2006), the workers ligate biotinylated hairpin adaptors to each end of a target DNA insert, where after the molecule is circularized by ligating the adaptor sequences together to bring the original target DNA terminus in close proximity to each other, situating on either side of the newly juxtaposed pair of biotinylated adaptors. The circular molecule is then cleaved randomly to create exposed ends that are of random distance from the termini of the original target DNA insert. Linear DNA fragments so generated are recovered by avidin-affinity chromatography and are sequenced along its entire length.

Kobel et al (2007) made use of the next generation DNA sequencer, GENOME SEQUENCER FLX (Roche Diagnostics, Indianapolis, Ind.; 454 Life Science Corp, Bradford, Conn.) (commonly refer as a "454-sequencer") to derive the original terminal sequences of the target DNA inserts. However, the resulting products produced as described cannot be interrogated effectively on a SOLEXA GENOME ANALYZER (Illumina, San Diego, Calif.) (commonly refer to as "SOLEXA sequencer"), or on SOLiD sequencer (Applied Biosystems, Foster City, Calif.) of any next generation sequencing platforms that produce "short sequence reads". The generated DNA products of Kobel et al (2007) and Berka et al (2006) adopt the so called "outside-in" topology whereby the original termini ("outside") of the target DNA insert are orientated in an inverted position ("in") separated by a newly juxtaposed biotinylated adaptor pair, which is located randomly within the length of the resulting DNA fragment. As a consequence of the adopted "outside-in" topology compared to the original target DNA termini, sequence determination several hundred bases or more is necessary to sequence across the biotinylated adaptor pair and through the other side of the DNA product in order to determine the terminal sequences of the original target DNA fragment. The majority of products produced in this way are within the four-hundred-bp read length of the 454-sequencer. Short read DNA sequencers, such as the SOLEXA, enjoy a ten-fold or more lower operating cost over the 454-sequencer, but have typical supported read length of 50-base, which is not sufficient to interrogate the products produced by the method of Berka et al (2006) and Kobel et al (2007) with absolute precision. Berka et al (2006) described a variant of their approach whereby the type IIS restriction endonuclease Mme I is used to produce tags of approximately 20-base corresponding to the terminal sequence of original DNA insert. By this approach, the workers fixed the length of the tag to be in range of the DNA sequencing capability of the SOLEXA-type DNA sequencer. However, the tags are still in an "outside-in" topology and the fixed 20-base tags generated by Mme I digestion are simply too short to map unambiguously to complex genomes to be useful as a genomic tool or to aid sequence assembly. Moreover, a fixed tag of 20-base would not enjoy the recent improvements in read length of the next generation short-read DNA sequencers. Currently the supported SOLEXA read length is 50-base from each side of a DNA template, with expected increase to 76-base later in 2009.

The present invention overcomes the aforementioned limitations through: (1) the ability to produce GVT-pairs whereby the spacing of tag-pair members on the target DNA can be engineered from a kb or less to several hundreds of kb or more to tailor detection resolution to suit the analysis of different types of nucleic acids and to suit any given experimental design; (2) considerably more accurate and uniform spacing between tag-pair members for greater analytical precision; (3) the ability to produce genomic tag-pairs based on other criteria besides separation distance, such as the creation of tag-pairs based on the location and/or the relative separation distance of adjacent cleavable endonuclease sites for improved interrogation of the target nucleic acid sample; and (4) adapting the methods of the present invention for use in the next generation massively parallel DNA sequencers for far greater economy. By adopting a so termed "outside-out" topology, whereby the juxtaposed terminal sequence tags (GVT-pairs) retain the same spatial orientation as the termini of the original target DNA insert and through the use of frequent cutting type II restriction endonucleases to generate GVTs of an average length of 100-200-bp, the SOLEXA "pair-end-read" platform can be translated directly into ever longer GVT sequences that are limited only by the actual read length of the instrument.

BRIEF SUMMARY

The present invention relates to systems, methods, compositions, vectors, vector components and kits to create pairs of linked genomic sequence tags and the rapid generation of high-resolution genomic maps. The invention creates pairs of short juxtaposing sequence tags termed Genomic Variation Tags (GVTs), where constituent members of a GVT-pair are of a user defined separation distance, and/or are markers to positions that demarcate cleavable adjacent sites for one or more different restriction endonucleases along the length of a nucleic acid molecule under investigation.

When individual GVTs of a GVT-pair are aligned computationally onto a reference sequence, any discordance with their expected identity, separation distance and/or orientation from the reference sequence denotes the presence of one or more fine-structural-differences between target and reference nucleic acids in the region spanned by the GVT-pair. In this way a comprehensive library of GVT-pairs represents a high-resolution genomic profile that can be used to generate high-resolution structural maps to identify fine-structural-variations between nucleic acid populations. Another aspect of the invention enables the user to define and to alter the separation distance on a nucleic acid population tagged by the GVT-pairs, thus allowing the creation of GVT-pair libraries that are tailored to detect fine-structural-variations at different spatial resolutions and physical coverage. Another aspect of the invention produces GVT-pairs that are markers to positions immediately proximal to pairs of adjacent and cleavable recognition sites for one or more different restriction endonucleases along the length of a nucleic acid population under investigation. As such, the present invention could be used to study the methylation status of a DNA population through the generation of sequence tags generated by differential digestion using methylation sensitive restriction endonucleases. Another aspect of the invention produces GVT-pairs that are markers to pairs of adjacent and cleavable recognition sites for one or more different restriction endonucleases and that are separated by a user defined distance along the length of a nucleic acid population under investigation. Another aspect of the invention provides methods, vectors, and DNA backbones for the creation of GVT-pairs of up to ~50-kb or more separation distance on a target DNA. Yet another aspect of the invention provides methods to produce GVT-pairs that can be sequenced efficiently on the next generation massively parallel DNA sequencers. For a review of the next generation DNA sequencers refer to Morozova and Marra (2008), and Mardis (2008).

According to one aspect of the present invention, DNA of a target population for analysis is fragmented either randomly or at defined sites. Fragmented target DNA insert is ligated into a suitable vector or a DNA backbone, whereby the ligated target insert is digested with one or more frequent cutting type II restriction endonucleases, cleaving the insert at a useful distance from each terminus causing the release of the intervening sequences to yield a pair of GVTs that are still attached to the undigested vector or DNA backbone. Typically, digestion with a frequent cutting type II restriction endonuclease with a four-base recognition site produces GVT of 100- to 200-bp length, corresponding to the average distance between the end of the target DNA insert and the location of the first cleavage site. The newly created vector-GVT complex is re-circularized by ligating the GVTs together to produce a GVT-pair representing juxtaposed terminal regions that are in the same relative orientation as the original target DNA insert. The GVT-pair are released from vector or DNA backbone by digestion at restriction endonuclease sites flanking the GVT-pair or by the use of PCR employing suitable primers that flank the GVT-pair. When the sequence of individual GVTs of a GVT-pair are aligned computationally onto a reference sequence, any discordance with either their expected identity, separation distance or orientation with those aligned on the reference denotes the presence of one or more fine structural differences between target and reference nucleic acids in the region spanned by the GVT-pair. Thus, the tabulated sequences of a plurality GVT-pairs constitute a detail genomic profile of the target nucleic acid population in respect to the reference sequence. Accordingly to yet another aspect of the present invention, fragmented target DNA is cloned into novel cosmid vectors, pSLGVT-28, pSLGVT-35, pSLGVT-36, pSLGVT-37, or pSLGVT-38 for GVT-pair production of 45- to 50-kb separation distance for sequence determination using the next generation SOLEXA, SOLiD or 454-DNA sequencers. These and other aspects of the invention will become evident upon reference to the following detailed description. hi addition, various references (including patents, patent applications and journal articles) are identified below and are incorporated by reference herein.

Useful utilities offered by the invention or derived products thereof include but are not limited to the rapid construction of high-resolution genomic maps that can be used to: (1) identify fine-scale-variations of the genome that contribute to human diversity and might be causal to disease, disease progression or disease susceptibility and other observed traits for use as diagnostics or as targets for therapeutic intervention; (2) enable the design and creation of oligonucleotide microarray or other assay methods for rapid and massively parallel interrogation of fine-structural-variants in DNA samples for medical diagnosis, genotyping, and other such useful applications; (3) facilitate accurate and rapid DNA assembly from whole genome or shotgun DNA sequencing approaches; (4) identify fine-structural-variations of RNA transcripts resulting from differential RNA processing to aid genomic annotation, functional genomic studies, and potential disease diagnosis; (5) create genomic profiles to facilitate comparative genomics and phylogenic studies and to aid differential identification of closely related organisms; and (6) create genomic profiles of related strains, races, biotypes, variants, breeds or species to identify genomic elements that might be causal to any observable phenotypes of academic, medical or of commercial interest.

DETAILED DESCRIPTION

The present invention provides novel improved high throughput methods, vectors, and vector components to screen and to identify fine-structural-variations in nucleic acid populations. The invention comprises an in vitro and in vivo method of creating juxtaposing sequence tags (GVTs) where two constituent members of a tag pair (GVT-pair) are unique positional markers of a defined separation distance and/or are markers of nucleic acid positions that demarcate adjacent cleavage sites for one or more different restriction endonucleases along the length of a plurality of target nucleic acid molecules. The method comprising: fragmenting the target nucleic acid molecule to form target DNA insert; ligating the target DNA insert to a DNA vector or a backbone to create a circular molecule; digesting the target DNA insert with one or more nuclease, preferably a frequent cutting type II restriction endonuclease to cleave the target DNA insert at a distance from each end of the target DNA insert thereby to create two sequence tags (GVTs) comprising terminal sequences of the target DNA insert that are attached to an undigested linear vector or DNA backbone; and recircularizing the linear vector or the DNA backbone with attached GVTs to obtain a circular DNA molecule containing a GVT-pair having two juxtaposed GVTs; GVT-pair DNA is recovered by nucleic acid amplification or digestion with restriction endonuclease having sites flanking the GVT-pair.

When individual GVTs of a GVT-pair are aligned computationally onto a reference sequence, any discordance with their expected identity, separation distance and/or orientation from the reference sequence denotes the presence of one or more fine-structural-differences between target and reference nucleic acids in the region spanned by the GVT-pair. By this method, a comprehensive library of GVT-pairs represents a high-resolution genomic profile that can be used to generate high-resolution structural maps to identify fine-structural-variations between nucleic acid populations and for the creation of genomic scaffolds to aid genomic assembly and structural analysis.

1. Preparation And Fragmentation of Nucleic Acids for Production of GVT-Pairs

As described herein, the present invention provides methods to produce high-resolution genomic maps that can be used to characterize and to aid the assembly of unknown genomes or to identify fine-structural-variations between target populations of nucleic acids to reference sequences. Target nucleic acids suitable for analysis include but are not limited to: genomic DNA of eukaryotic and prokaryotic organisms; microbial DNA, plastid DNA; plasmid and phagemid DNA; viral DNA and RNA; complementary DNA (cDNA) derived from ribonucleic (RNA); and DNA produced by in vitro amplification such as by PCR among others. Methods for DNA isolation from aforementioned sources, synthesis of cDNA from RNA and the amplification of nucleic acids are known to those skilled in the art.

For certain embodiments, the physical distance spanned by the GVT-pair along the length of the target DNA determines the resolution level for analysis. The smaller the spacing between GVTs, the higher is the spatial resolution for mapping and for detecting fine-structural-variations within a target population of nucleic acids. Larger GVT-pair spacing requires fewer GVT-pairs to provide physical coverage a DNA sample of a given complexity but with a concomitant decrease in spatial resolution to detect small genomic structural variants. Large GVT-pair spacing spans large repetitive regions to facilitate de novo genomic assembly and the analysis of large structural alternations in DNA. The ability to produce GVT-pairs of 5-, 10-, 25-, 50-, 100-kb, or more separation distance allows the end-users to choose functional tradeoffs between GVT spacing, resolution level required to detect different types of DNA structural variations, and the number of GVT-pairs needed to provide adequate physical coverage for a genome of a given complexity. The optimal number and the proportion of GVT-pairs of different spacing can be modeled computationally for specific applications.

As described above, the physical length of target DNA insert used for the construction of GVT-pairs governs the separation distance between resident GVTs of a GVT-pair, thus setting the resolution level for the analysis. Methods to create and to purify a near homogeneous size population of fragmented nucleic acid molecules are described in the art. Fragmenting a target DNA population to a desired insert length can be accomplished enzymatically under conditions of partial or complete digestion with a variety of restriction endonucleases. The use of restriction endonuclease with recognition sites of six or greater base pairs are useful to produce longer DNA fragments. The use of one or more restriction endonucleases with different sensitivity to DNA methylation can be used to assess the DNA methylation status of the target DNA population. The use of frequent cutting type II restriction endonucleases such as Mbo I, Hae III, and the like, which cut DNA once on average every 256-bp (based on random distribution and equal representation of the four bases in the target DNA), is known in the art for producing varied sizes of DNA fragments by partial digestion. The use of restriction endonuclease CviJ I under relaxed conditions, which cleaves DNA at GC dinucleotide positions (Fitzgerald et al, 1992), is particularly useful under partial digestion conditions to produce a useful continuum of DNA fragment sizes. In some embodiments, randomly generated DNA fragments are useful. Methods for generation of random DNA fragments include: (1) digestion with bovine pancreatic deoxyribonucleic acid nuclease I (DNase I), which makes random double-strand cleavages in DNA in the presence of manganese ions (Melgar and Goldthwait, 1968; Heffron et al, 1978); (2) physical shearing (Shriefer et al, 1990); and (3) sonication (Deininger, 1983).

Conditions for partial enzymatic digestion are determined empirically, varying one or more parameters of reaction volume, enzyme concentration, and enzyme to substrate ratio, incubation time or temperatures. For high-resolution analysis requiring a GVT separation of 5-kb or less, fragmentation methods that are not sequence dependent is preferred. Bovine pancreatic DNase I makes random double-strand cleavages in DNA in the presence of manganese ions (Melgar and Goldthwait, 1968; Heffron et al, 1978) and can be used for this purpose. Likewise, DNA fragmentation by mechanical means such as sonication, or the selective application of shear forces can also be used. The HYDROSHEAR instrument (Genomic Solutions Inc, Ann Arbor, Mich.) or the COVARIS (Covaris Inc, Woburn, Mass.) instrument employing Adaptive Focused Acoustics are particularly useful for generating random DNA fragments of a defined size range. Random DNA fragments can also be generated through the use of random primers during cDNA synthesis or during PCR, alone or in combination with the other fragmentation methods described. The progress of fragmentation to yield the desired length product is easily monitored by gel electrophoresis. Following generation of a suitable DNA size-distribution, $T_4$ DNA polymerase is used to repair or to make blunt the target DNA ends in preparation for blunt-end ligation to vector, DNA backbone, or GVT-adaptors for the production of the GVT-pairs of the present invention. In cases where DNA is fragmented by partial or complete digestion with one or more endonucleases leaving cohesive ends, repair is not necessary but the design of the GVT-adaptor, vector, or DNA backbone will need to accommodate the particular cohesive ends generated by the fragmentation enzyme. Since ligation of target DNA inserts to other target DNA inserts destroys the co-linearity of the sample and undermines the construction of genomic maps, the 5' phosphate groups of the target DNA are removed by a phosphatase to prevent the creation of chimeric DNA inserts during ligation to the GVT-adaptor or to the DNA backbone.

2. Size Fractionation and Purification of Size-Selected DNA

For certain embodiments, dephosphorylated DNA inserts are fractionated by gel electrophoresis or by high performance liquid chromatography (HPLC) to yield purified DNA inserts of a desired size. Poly-acrylamide gels are best used for fractionation of DNA from 50-bp to 1-kb. For fragment sizes of ~250-bp to ~50-kb, 0.4% to 3% agarose gels are suitable. Pulsed field gel electrophoresis is suitable for fractionating DNA from ~10-kb to several hundreds of kb in size. These procedures are described in references therein (Rickwood and Hames (eds), In: *Gel Electrophoresis of Nucleic Acids—A Practical Approach*, Oxford University Press, New York, 1990; Hamelin and Yelle, 1990; Birren and Lai, In: *Pulse Field Electrophoresis: A Practical Guide*, Academic Press, San Diego, 1993). DNA is sized with the use of suitable size markers electrophoresed in parallel with the sample and are visualized by staining. Gel slices containing DNA of a desired size are excised with a scalpel, after which the DNA is recovered from the gel matrix by electro-elution or by enzymatic or chemical degradation of the gel matrix. The recovered DNA fragments for analysis should be near homogeneous in size. Gel systems and electrophoretic conditions for maximizing separation resolution are known in the art. Two or more cycles of gel electrophoresis may be used to obtain greater sample size homogeneity. Sample with size variance of more than 2.5% to 5% from the mean length may contribute to unacceptable noise for use by the present invention.

3. Design of GVT-Adaptor and Ligation of Target DNA to Vector or DNA Backbone

In some embodiments, the target DNA insert is first ligated to adaptors to facilitate its ligation to a suitable vector or to a DNA backbone. In other embodiments, the target DNA insert is ligated directly to a vector or to a DNA backbone without using adaptor intermediates. In yet other embodiments, individual adaptors are first ligated to each ends of a target DNA whereupon the free ends of the newly ligated adaptors are recircularized to form a functional DNA backbone for the subsequent generation of a GVT-pair. Adaptors may incorporate moieties such as biotin groups to facilitate affinity purification of the desired DNA products. Adaptors may also incorporate restriction endonuclease recognition sites for the excision of the generated GVT-pair from the DNA backbone or the incorporation of nuclease recognition sites for type IIS, IIG or type III endonucleases to create the GVT by cleavage of the ligated target DNA insert. For GVT generation where the target DNA insert is ligated directly to the vector or to the DNA backbone, the appropriate recognition sites for the aforementioned type IIS, IIG or type III restriction endonucleases may be incorporated into the design of the vector or the DNA backbone. Another aspect of the present invention makes use of one or more type II restriction endonucleases to digest the ligated target DNA insert to create GVTs that are attached to each ends of a vector or DNA backbone, where the said vector or the DNA backbone are designed to be free of those digestion sites and remains undigested.

Those skilled in the art would realize the existence of a plurality of GVT-adaptor designs suitable for execution of the present invention. In general, a suitable GVT-adaptor comprises the following material properties: (1) a short top strand and a short bottom strand of 5' phosphorylated oligonucleotides capable of stable complementary base-pairing to yield a two strand structure; (2) one end of the GVT-adaptor has a cohesive extension (non palindromic is preferred) that ligates to a vector, to a DNA backbone, or to another adaptor having the complementary sequence; (3) the other adaptor end has a blunt-end structure or other suitable end structures to enable efficient ligation to the target DNA fragments (dephosphorylated target DNA is preferred); (4) for some embodiments, the end of the adaptor flanking the target DNA insert may bear a suitable type IIS, type IIG or type III restriction endonuclease recognition site in an orientation such that the site directs cleavage within the target DNA at a fixed and useful distance from the target DNA terminus to produce a GVT (For reviews of the type IIS, IIG and III restriction endonucleases, see Sistla and Rao (2004), Bujnicki (2001), Szybalski et al (1991); and (5) the adaptor may bear a second restriction endonuclease site for excising the created GVT-pair from the vector.

Those of skill in the art know methods for ligation of adaptor to DNA insert and for general ligation of nucleic acid molecules. See, for example, Ausubel et al (eds) (In: *Short Protocols in Molecular Biology*, 3$^{rd}$ Ed, John Wiley & Sons, New York, 1995). Typical ligation conditions for efficient blunt-end ligation of adaptor to DNA insert call for a ~50 to several hundred-fold molar excess adaptor to target DNA, high T$_4$ DNA ligase concentration, or the inclusion of a volume exclusion agent such as polyethylene glycol (Hayashi et al, 1986; Pheiffer and Zimmerman, 1983; Zimmerman and Pheiffer, 1983). Efficient ligation of adaptor to cohesive end target DNA requires~five-fold molar excess. GVT-adaptor-ligated DNA inserts are passed through a CHROMOSPIN column (Clontech, Mountain View, Calif.) to remove excess adaptors before purification and size-selection by gel electrophoresis. To generate GVT-pairs by intra-molecular ligation, the purified adaptor-ligated target DNA inserts are ligated into one of several plasmid vectors and DNA backbones as described below.

According to an aspect of the present invention, any restriction endonucleases, preferably a frequent cutting type II restriction endoculease, that preferentially cleave the target DNA insert and not the vector, the DNA backbone or any adaptors to which the target DNA is ligated, are suitable for use in the generation of GVTs and GVT-pairs. REBASE, the restriction enzyme database, provides information of the type II restriction endonucleases, isoschizomers, neoschizomers, recognition sequences, commercial availability and references (rebase.neb.com). Preferred type II restriction endonucleases are those that cut the target DNA insert frequently, such as enzymes that recognize 4-base pair sites, thereby creating GVT of average lengths of 100- to 300-bp. Type II restriction endoucleases FspB I or Csp6 I, alone or in combination, are particularly suited for use by the present invention to generate GVTs since these two enzymes cut frequently and produce the identical complementary cohesive ends allowing the direct production of a GVT-pair of the present invention by intra-molecular ligation without modifications to the ends. Other restriction endonucleases that only cleave the target DNA insert but not the vector, the DNA backbone, or the adaptors to which the target DNA insert is attached, are considered within the scope and spirit of the present invention for the production of GVTs and GVT-pairs.

4. Vectors and DNA Backbones for GVT-Pair Production

In some embodiments where large GVT-spacing is required, it may be desirable to propagate the target DNA in a host cell prior to the creation of the GVT. Rearrangement or loss of target DNA segments containing AT- or GC-rich sequences, repeats, hairpins, strong promoters, toxic genes and other problem sequences when propagated in host cells are of concern. DNA rearrangements and other cloning artifacts can be mistaken for structural variations in the target nucleic acid. Moreover, cloning bias can limit the size of inserts and can under-represent important regions of the genome under study. This problem was addressed recently with the development of fosmid and BAC vectors with conditional amplification (Szybalski, U.S. Pat. No. 5,874,259) where propagation of DNA is kept at one to two copies per host cell until induced to higher levels for analysis. Improved stability of genomic inserts of 15-kb to over 100-kb was reported and conditional amplification vectors are now in routine use for genomics studies. Conditional amplification fosmid/BAC vectors such as pCCIFOS (Epicentre, Madison, Wis.) and pSMART-VC (Lucigen, Middleton, Wis.) and their variants are suitable for use in GST-pair production of GVT-spacing from 10-kb to 200-kb. However, use of conventional low-copy plasmid vectors appeared to be sufficient for stable maintenance of large DNA fragments without the need of BAC, PAC or fosmid type vectors (Feng et al, 2002; Tao and Zhang, 1998). The pSMART series of vectors offers low copy number propagation and has the added feature of having transcription terminators on the vector to reduce the potential effects of transcriptional interference, which might further improve DNA stability (Mead and Godiska, U.S. Pat. No. 6,709,861). For GVT-pair production of GVT-spacing of 10-kb or more, a variety of established and widely used low copy plasmid-based vectors are suitable to produce GVT-pairs, including: pBR322 (Bolivar et al, 1977), pACYC177 (Chang and Cohen, 1978) and others described in the present disclosure.

For the execution of the invention, vector or DNA backbone to which the target DNA is ligated must be free of cleavage sites for the restriction endonuclease used to generate the GVT from the target DNA insert. Cleavage of the vector or the DNA backbone would destroy the spatial linkage of the GVTs, hence it would prevent the creation of the GVT-pair by intra-molecular ligation. Vector backbone can be made free of unwanted restriction sites by site-directed mutagenesis employing standard methods. See, for example: McPherson (ed) (In: *Directed Mutagenesis—A Practical Approach,* Oxford University Press, New York, 1991) and Lok (U.S. Pat. No. 6,730,500). Typically, a substantial portion of a vector DNA or DNA backbone can be altered by single base-pair change to eliminate unwanted restriction endonuclease recognition sites without due effects on functionality. Within protein coding sequences, single nucleotide changes are targeted to the codon wobble positions to maintain native protein coding. Changes made elsewhere on the vector or the DNA backbone would require functional validation before use. Many restriction endonucleases are sensitive to methylation of their recognition sites, in particular, methylation at the 5-carbon position of deoxycytosine can render those sites on the vector or the DNA backbone free from digestion. DNA methylation can be accomplished through direct incorporation of 5-methy-dCTP by PCR, passage of DNA through appropriate host cells with different restriction modification systems, or by use of specific methylases to render restriction sites on the vector or DNA backbone retractile to enzymatic cleavage. REBASE, the restriction enzyme database, provides information of the methylation sensitivity of restriction endonucleases, (rebase.neb.com).

DNA backbone to create GVTs and GVT-pairs by intra-molecular ligation can also be created by direct chemical synthesis to any desired specification. Subsequent large-scale production of a DNA backbone can be produced by chemical synthesis or in part or in whole by PCR from a template. The DNA backbone may contain replication origin and selection marker for propagation in microbial host. Alternatively, the DNA backbone may contain only a minimal sequence comprising essentially a pair of spatially linked adaptors. Individual adaptors are first ligated to ends of the target DNA insert whereupon the free adaptor ends are then ligated together to reconstitute a DNA backbone thereby creating a circular molecule for GVT production. In some other embodiments, the adaptors may incorporate a recognition site for a type IIS, IIG or a type III restriction endonuclease site in an orientation to direct cleavage of the target DNA at a defined distance from the target DNA end to generate the GVT. Biotin and other moieties can also be incorporated into the DNA backbone to enable affinity purification of DNA intermediates in the different steps of in vitro GVT-pair production. One particularly useful design comprises a synthetic DNA backbone that is free of all or most of the sixteen possible four-base-pair palindromes. Such a DNA backbone would allow the generation of GVTs by digestion of the ligated target DNA insert with nearly any four-base recognition restriction endonucleases, alone or in combination without cleavage to the DNA backbone or adaptor. Another particularly useful DNA backbone design incorporate sequences that are compatible with DNA amplification and sequencing primer binding for use in the next generation DNA sequencing platforms for massively parallel high throughput DNA sequencing of GVT-pairs. The DNA backbone is preferably long enough either to provide primer binding sites for the amplification of the created GVT-pair, to effect affinity purification, to enable efficient attachment (ligation) to the target DNA, or to at best be a unique identifier in providing a reference point.

5. GVT-Pair Production Vectors pSLGVT-1, pSLGVT-2, pSLGVT-28, pSLGVT-35, pSLGVT-36, pSLGVT-37, AND pSLGVT-38

The pSLGVT series of vectors comprise two chemically synthesized DNA modules to provide the basic maintenance functions of drug selection and plasmid replication, respectively. The vector modules bear terminal unique type IIS restriction endonuclease sites that create unique asymetric cohesive ends to allow rapid future reconfiguration of the vector components to add or substitute modules or DNA cassettes for new functionalities.

The first vector module comprises a modified P15A origin of replication. Plasmids bearing the P15A replicon propagate at a low number of approximately 15 copies per host cell (Sambrook et al, In: *Molecular Cloning—A Laboratory Manual*, $2^{nd}$ Ed, CSH Laboratory Press, Cold Spring Harbor, N.Y., 1989), thereby optimizing the stability of cloned genomic inserts. The Mme I sites within the P15A replicon were eliminated by making every possible single nucleotide change that abolishes the two sites and each mutant was screened for replication competency to yield a functional "P15A-m replicon module" for the construction of pSLGVT-1. The EcoP15 I site in the P15A replicon is eliminated by a simple single base alteration to yield the "P15A-e module" for the construction of plasmid pSLGVT-2.

The second vector module comprises a modified Kan gene from transposon Tn903 conferring resistance to antibiotic Kanamycin (Grindley et al, 1980). Taking advantage of the wobble position and conforming to the optimal codon usage in *E. coli* whenever it is possible, four Mme I sites along with two Nci I and Nsi I sites, and single sites for Esp3 I, Pst II, and Hind III were eliminated within the coding region of the Kan gene to yield the "Kan module".

Cosmid vector, pSLGVT-28, offers unique benefits for the production of GVT-pairs of 45- to 50-kb spatial separation for use in the next generation DNA sequencing platforms. GVT-pairs of that spacing are particularly useful in providing efficient physical coverage of genomic DNA to identify fine structural variations and for spanning large regions of repetitive DNA for producing genomic scaffolds to facilitate de novo sequencing of complex genomes. pSLGVT-28 is derived from pSLGVT-2, through: (1) the incorporation of a COS site from phage lambda for in vitro phage packing, enabling efficient and accurate biological size-selection of target DNA inserts to create complex libraries of GVT-pairs of precise ~45- to 50-kb separation; (2) the elimination of all FspB I and Csp6 I restriction endonuclease sites on the vector by site-directed mutagenesis allowing the creation of GVTs and subsequent GVT-pairs by digestion of the ligated target DNA insert with those enzymes, alone or in combination; and (3) the creation of a cloning site for target DNA that is situated between the Illumina Corporation's "Adaptor-A" and "Adaptor-B" sequences to allow solid-phase DNA amplification and sequencing of the created GVT-pair using the SOLEXA "pair-end-read" sequencing platform.

Efficient generation of GVT-pairs of 45- to 50-kb separation in conjunction with massively parallel DNA sequencing on the SOLEXA "pair-end-read" platform offers tremendous improvements in cost and efficiency over the low-throughput fosmid paired-end mapping method of Tuzun et al (2005) for identifying genomic variations and for the production of long-range scaffolds to aid DNA assembly.

Cosmid vector pSLGVT-35 is a derivative of pSLGVT-28, whereby a pair of inverted BciVI restriction endonuclease sites is situated between the Illumina Corporation's SOLEXA "Adaptor-A" and "Adaptor-B" sequences. BciVI is a type IIS restriction endonuclease producing a 3' extension of one base situating six-base pairs from the enzyme recognition site. BciVI digestion is used to produce a single 3' thymine overhang flanking Adaptors-A and -B on the vector to receive adenine tailed target DNA inserts prepared in accordance to the SOLEXA DNA preparation kit for DNA template preparation.

Cosmid vector pSLGVT-36 is a derivative of pSLGVT-28, whereby the SOLEXA Adaptor-A and Adaptor-B sequences are replaced with Adaptor-A and Adaptor-B from Roche Diagnostics' 454-platform (GS FLX TITANIUM) for direct sequence determination of GVT-pairs on that platform.

Cosmid vector, pSLGVT-37 is another derivative of pSLGVT-28, whereby the SOLEXA Adaptor-A and Adaptor-B are replaced with Internal Adaptors from Applied Biosystems's SOLiD "Mate-Pair Library" system for direct sequence determination of GVT-pairs on the SOLiD platform.

Cosmid vector pSLGVT-38 is yet another derivative of pSLGVT-28, whereby SOLEXA Adaptor-A and Adaptor-B are replaced with Roche Diagnostics' 454-Internal Adaptors to generate GVT-pairs adapting an "outside-in" configuration for sequencing on the 454-platform.

6. GVT-Pair Production

In certain embodiments, a population of target DNA for GVT-pair production is fragmented randomly by mechanical or enzymatic means to produce fragments of a desired size for GVT-pair production. In other embodiments, a target DNA population is digested to completion with one or more restriction endonucleases in separate reactions or in combination to cleave target DNA at specified sites. In yet another embodiment, target DNAs are digested to completion with one or more restriction endonucleases and are then fractionated to a desired size. For target DNA digested with enzymes that create cohesive ends, the dephosphorylated target DNA may be cloned directly into a suitably modified vector or DNA backbone. Fragmented target DNA having "ragged" ends are repaired using $T_4$ DNA polymerase or mung bean nuclease and are then dephosphorylated to prevent the creation of chimeric target DNA inserts. Likewise, target DNA bearing cohesive ends is also dephosphorylated to prevent the creation of chimeric inserts. Where ligation of target DNA to vector or DNA backbone is carried out with the use of adaptors, CHROMASPIN columns (Clontech, Mountain View, Calif.) are used to remove unligated adaptor before ligation of adaptor-ligated target DNA to a GVT production vector. In certain embodiments, target DNA are size-selected to a desired length by gel electrophoresis or by other means prior to GVT-production.

As used herein, cosmid, fosmid, phagmid, BAC and other episomal elements are referred collectively as plasmids or as DNA backbones. Ligation conditions for optimizing intermolecular ligation of a vector or a DNA backbone to an insert followed by intra-molecular ligation to yield a circular molecule have been described for DNA segments over a range of fragment lengths (Collins and Weissman, 1984; Dugaiczyk et al, 1975; Wang and Davidson, 1966). General methods for ligating nucleic acid molecules, transfection into host cell and for construction of plasmid-based libraries are known to those who are skilled in the art. See, for example, Sambrook et al (In: *Molecular Cloning: A Laboratory Manual* 2$^{nd}$ Ed, CSH Press, New York, 1989); Ausubel et al, (eds) (In: *Short Protocols in Molecular Biology*, 3$^{rd}$ Ed, John Wiley & Sons, New York, 1995); Birren et al (In: *Bacterial Artificial Chromosomes in Genome Analysis—A Laboratory Manual*, CSH Press, New York, 1999). Ligated target DNA is introduced into host cells by electroporation or by transfection. Alternatively, target DNA inserts of 45- to 50-kb ligated onto a suitable cosmid vector such as, pSLGVT-28, pSLGVT-35, pSLGVT-36, pSLGVT-37, pSLGVT-38 or their derivates, are transduced into host cells after in vitro phage packaging using an appropriate commercially available packaging extract (Stratagene, La Jolla, Calif.). Propagation of methylated target DNA such as genomic DNA or cDNA synthesized by certain protocols that make use of methylated nucleotide analogues requires host cell strains with inactive mcr and mrr alleles. Suitable host strains include: 10G (Lucigen, Middleton, Wis.); XL1-Blue MR and XL2Blue MRF' (Stratagene, La Jolla, Calif.). Electroporated, transfected or transduced cells are plated onto 10 cm diameter agar plates at a density of ~20,000 to 50,000 colonies per plate under the appropriate drug selection to yield the primary library. An alternative method is to grow the transduced or tranfected cells in liquid culture while exercising care not to overgrow cells to encourage undesirable clonal selection. The total number of clones under culture should reflect the number of GVT-pairs required by the study design. Cells are harvested and the plasmids isolated for the subsequent step described below.

In an aspect of the invention, pSLGVT-28, pSLGVT-35, pSLGVT-36, pSLGVT-37, pSLGVT-38, and any other functionally equivalent vectors or DNA backbones bearing target DNA insert are digested to completion with FspB I or Csp6 I (Fermentas Inc, Hanover, Md.) to generate GVTs. The resulting digestion cleaves the insert DNA to generate the GVT without cleavage to the attached vector or DNA backbone. GVTs generated in this manner are variable in size, dependent on the average frequency of cut sites within the target DNA and the distance of the first cut site from the target DNA termini. GVTs produced by FspB I or Csp6 I digestion of randomly fragmented human DNA inserts are expected to have an average length of 100- to 200-bp. Linearized vector or DNA backbone with the newly created GVTs attached are purified away from the milieu of digested insert DNA fragments, by gel electrophoresis or by affinity chromatography. Purified linear products are circularized to yield the primary GVT-pair library. GVT-pairs can be recovered from the circularized templates by DNA amplification for direct DNA sequencing. Alternatively, circularized vector bearing GVT-pairs are introduced into host cells and plated at a density of ~20,000 to 50,000 colonies per 10 cm plate or are grown in liquid culture under selection to yield a primary plasmid GVT-pair library. Purified plasmids from the plasmid primary GVT-pair library are digested with enzyme that cleaves both sides of the GVT-pairs to excise the GVT-pair from the vector for direct DNA sequencing.

7. In vitro GVT-Pair Production

It is considered within the scope and principle of the present invention to produce GVTs and GVT-pairs in vitro without propagation steps through a host cell. Generally, DNA backbones suitable for generation of GVTs without propagation through a host cell should be at least 50- to 100-bp or more in length in order to have sufficient segmental flexibility to undergo intra-molecular ligation to yield a circular molecule for creating the GVT-pair. DNA backbone for in vitro GVT-pair production need not necessarily contain a replication origin or a drug selection marker. Such DNA backbones should possess suitable PCR primer binding sites flanking the GVT-pair for amplification of the created GVT-pair. The DNA backbone may be derived in part or in whole from restriction endonuclease digestion of an engineered plasmid. Suitable DNA backbones can also be produced, in part or in whole by PCR, or by direct chemical oligonucleotide synthesis. In cases where the DNA backbone is derived from PCR or from chemical synthesis, modified nucleotides can be incorporated into the DNA backbone for additional functionality. For example, a biotin moiety can be incorporated into the DNA backbone to enable affinity purification of DNA intermediates in the different steps of in vitro GVT-pair production. One particularly useful DNA design comprises a DNA backbone that is essentially free or depleted of the sixteen possible four-base-pair long palindromes, allowing the generation of GVTs by digestion of attached target DNA insert with nearly any four-base recognition restriction endonucleases. DNA backbone may also include primer binding site and other sequences for clonal amplification of DNA templates for DNA sequencing on the next-generation DNA sequencers.

Although in vitro GVT-pair production offers the possibility to generate more complex libraries of GVT-pairs and avoids the inconvenience of a propagation step through a microbial host cell, however, a propagation step in a microbial host is advantageous in some applications where the presence of artifacts needs to be minimized. A major source of artifacts stems from the creation of unwanted molecules where two different target DNA molecules are ligated to each end of a vector or a DNA backbone. Another source of artifacts is created during the intra-molecular ligation step to generate the GVT-pair, where GVTs of two different vectors or DNA backbones are joined by inter-molecular ligation. Specifically, GVTs from two different target DNAs are joined to create an artifact GVT-pair following PCR amplification. General ligation conditions for optimizing inter-molecular and intra-molecular ligation have been described for DNA segments over a range of fragment lengths (Collins and Weissman, 1984; Dugaiczyk et al, 1975; Wang and Davidson, 1966) to derive optimal conditions to produce circular molecules for in vitro GVT-pair production. Nevertheless, the chance occurrence of unwanted ligation events could not be entirely eliminated in practice. However, the majority of artifact GVT-pairs can be purged through a passage step in bacteria. Linear DNA or large concatenated DNA vectors are not transformed and propagated efficiently in microbial cells, making this approach the method of choice for applications such as de novo genomic assembly where sequence co-linearity of GVT-pairs is paramount.

8. Sequencing GVT-Pairs Using Next Generation of Massively Parallel DNA Sequencers There are currently three new commercial systems available for ultra-high-throughput, massively parallel DNA sequencing: The GENOME SEQUENCER FLX system, commonly known as 454-sequencing (Roche Diagnostics, Indianapolis, Ind.); SOLEXA (Illumina, San Diego, Calif.); and the SOLiD system (Applied BioSystems, Foster City, Calif.). The throughput of these new instruments can exceed several billion base calls per run, a factor more than fifteen thousand-fold over the current generation of 96-lane capillary-electrophoresis-based sequencing instruments. The use of these new sequencing platforms for characterization of GVT-pairs is considered within the scope and principle of the present invention. GVT-pairs of the present invention can be sequenced on the new instruments without undue modification of the operational protocols.

The 454-technology is based on pyrosequencing chemistry carried out on clonally amplified DNA templates on microbeads individually loaded onto etched wells of a high-density optical flow cell (Margulies et al, 2005). Signals generated by each base extension are captured by dedicated optical fibers. A typical 454-instrument run comprises 500 thousand individual reads of 500-bases, a length sufficient to characterize a GVT-pair of the present invention.

Applied Biosystems' SOLiD platform for massively parallel DNA sequencing is based on sequential cycles of DNA ligation. By this approach, immobilized DNA templates are clonally amplified on beads, which are plated at high density onto the surface of a glass flow-cell where the sequencing reaction occurs. Sequence determination is accomplished by successive cycles of ligation of short defined labeled probes onto a series of primers hybridized to the immobilized template. A SOLiD instrument run comprises more than 100 million individual 50-base reads Sequencing templates for the SOLEXA platform are immobilized onto a proprietary flow cell surface where they are clonally amplified in situ to form discrete sequencing template clusters with densities up to ten-million or more template clusters per square centimeter. SOLEXA-based sequencing is carried out using primer-mediated DNA synthesis in a step-wise manner in the presence of four proprietary modified nucleotides having a reversible 3' dideoxynucleotide moiety and a cleavable chromofluor. The 3' dideoxynucleotide moiety and the chromofluor are chemically removed before each extension cycle. Cycles of step-wise nucleotide additions from each template clusters are detected by laser excitation followed by image capture from which base calling is made. A current instrument run comprises up to 100 million pair-end-reads of 76-base, is ideally suited to sequence GVT-pairs generated by frequent cutting FspB I or Csp6 I type II restriction endonuclease cleavage of target DNA.

Production of GVT-Pairs of 45- to 50-Kb Spatial Separation on the SOLEXA Platform Of the three major platforms, the SOLEXA is the only one where both template strands are present on the flow cell to enable direct sequencing from both ends of a DNA template. As such, the present invention is suited to the unique direct "pair-end-read" capability of the SOLEXA platform. When used with cosmid vectors pSLGVT-35 or its derivates, the present invention offers the ability to produce GVT-pairs of 45- to 50-kb spatial separation from a population of target DNA. The use of the head-full packaging mechanism of bacterial virus greatly improves the precision of target DNA sizing over what that could be achieved by the use of agarose gel separation alone. Accurate spacing of 45- to 50-kb provides economical physical coverage of the genome to identify fine-scale-variations and to span repetitive regions in the target DNA to facilitate the creation of genomic scaffold for de novo genomic sequencing. The present invention offers substantial improvements in economy and depth of physical coverage over the Fosmid paired-end mapping method of Tuzun et al (2005).

The SOLEXA Adaptors provide three sets of overlapping primer-binding sites: one set directs PCR amplification to produce progeny sequence templates flanked by Adaptor-A and -B sequences; a second set mediates solid phase isothermal amplification of the resulting progeny templates to generate template clusters that are immobilized on the surface of a sequencing flow cell; and (3) the last set provides binding sites for the sequencing primer on each of the two DNA strands. The present invention makes use of the pair-end-read capability of the SOLEXA platform to sequence created GVT-pairs. As exemplified by pSLGVT-35 and its derivatives, SOLEXA adaptors are engineered onto the DNA vector backbone, situating on each side of the target DNA cloning site. In this way, newly created GVT-pairs can be directly sequenced on the SOLEXA platform. A GVT-pair sequence of 152-base is derived from two separate 76-base single-reads from each ends of a DNA template. Effective read lengths of the FspB I and Csp6 I generated GVT-pair are expected as the SOLEXA read lengths improve from the current 76-base read. Supported single pair-end-reads of greater than 100-base is expected in late 2009.

pSLGVT-35 is a 2.6-kb vector comprising a Kanamycin selection marker, a low copy number P15A origin of replication for stable propagation of genomic DNA, and a COS site for lambda phage packaging. Cleavage sites on the vector for restriction endonucleases FspB I and Csp6 I were eliminated by site-directed mutagenesis, enabling use of these enzymes in the production of GVTs and subsequent GVT-pairs from a target DNA insert in accordance to the method of the invention. The target DNA cloning site is flanked by a pair of inverted BciVI restriction endonuclease sites situated immediately between the Illumina Corporation's SOLEXA "Adaptor-A" and "Adaptor-B" sequences on the vector. BciVI is a type IIS restriction endonuclease producing a 3' extension of one base situating six-base pairs from the enzyme recognition site. BciVI digestion of the vector at the pair of inverted sites produces a single 3' thymine overhang flanking Adaptors-A and -B to receive adenine tailed target DNA inserts prepared in accordance to the SOLEXA DNA template preparation kit.

Target DNA is sheared to fragment sizes of between 40- to 55-kb and the ends repaired with $T_4$-DNA polymerase and tailed with a single adenine nucleotide using exo minus Klenow polymerase in the presence of dATP. DNA fragments of 45- to 50-kb are purified from an agarose gel and are ligated onto thymine tailed pSLGVT-35 vector. Ligation of cosmid vector to target DNA is accomplished at equal molar ratio of linearized vector to target DNA insert and at a high-DNA concentration (typically 2- to 3-ug or more per ul total nucleic acids) to drive the production of long concatemers comprising alternating vector and target DNA fragments. The ligated product is packaged into phage particles using commercially available packaging extracts (Stratagene, La Jolla, Calif.). The propagation of methylated target DNA such as genomic DNA requires host cell strains with inactive mcr and mrr alleles. Suitable host strains include: 10G (Lucigen, Middleton, Wis.); XL1-Blue MR and XL2Blue MRF' (Stratagene, La Jolla, Calif.). Infected cells are plated onto 10-cm diameter agar plates at a density of 20,000 to 50,000 colonies per plate under the Kanamycin selection to yield a primary cosmid library comprising target DNA inserts of average 45- to 50-kb flanked on one side by SOLEXA Adaptor-A and the other side by SOLEXA Adaptor-B. An alternative method is to grow the infected cells in liquid culture while exercising care not to overgrow cells to encourage undesirable clonal selection. The total number of clones under culture should reflect the number of GVT-pairs required by the study design. Cells are harvested and cosmid DNA isolated for GVT-production. Purified cosmid DNA bearing target DNA insert is digested to completion with FspB I or Csp6 I. Digested products are passed through a CHROMASPIN 1000 (Clontech, Mountain View, Calif.) column to remove the bulk of the digested target DNA insert. The flow through material is electrophorsed on an agarose gel. DNA fragments of approximate 2.6- to 3-kb, corresponding to the intact linear cosmid vectors with two attached GVTs corresponding to the termini of the target DNA insert, are recovered from the gel. The recovered material is diluted to less than 25 ng/ul for intra-molecular ligation to create the GVT-pair. The junction of the newly juxtaposed GVTs is demarcated by the reconstitution of the restriction endonuclease site for the enzyme used to generate the GVTs and sets the boundary of the GVTs within the GVT-pairs for the subsequent data analysis. The resulting GVT-pair is recovered from the vector backbone by DNA amplification using primers to SOLEXA Adaptors-A and -B. The recovered GVT-pairs, flanked by SOLEXA Adaptors, are amplified on the surface of the flow cell for pair-end sequencing on the SOLEXA platform.

It is considered within the scope and the principle of the present invention to produce GVTs and GVT-pairs of other spatial separation with or without the use of in vitro virus packaging, as well as with or without a propagation step through a host cell. In the latter case, target DNA insert bearing SOLEXA Adaptors at each end are cloned into a suitable DNA backbone bearing a COS site and is then packaged into phage heads using commercially available packaging extracts (Stratagene, La Jolla, Calif.) as described. The DNA backbone can be labeled with a purification moiety, such as biotin, to facilitate affinity purification of the desired DNA product. Unpackaged DNA is degraded with nucleases where upon the protected packaged DNA is purified by phenol extraction. The target DNA insert in the resulting circular DNA molecule is cleaved with the appropriate restriction endonuclease (FspB I or Csp6 I) to produce a linear molecule comprising the DNA backbone with the attached GVTs. The desired linear DNA is purified by affinity chromatography. The exposed GVT ends are recircularized by intra-molecular ligation with DNA ligase to produce the GVT-pair as well as to seal the DNA at the COS site to yield a stable circular molecule. GVT-pairs are recovered by PCR from the ligation mixture using Adaptor-A and -B primers for SOLEXA "pair-end" sequencing.

Production of GVT-Pairs of 45- to 50-kb Spatial Separation on the 454-Platform Outside-Out Topology The present invention is particularly well suited to produce GVT-pairs for sequencing on Roche Diagnostics' 454-platform without employing the method of Berka et al (2006) (U.S. Patent Application 2006/0292611) and Kobel et al (2007). The method of Berka et al (2006) and Kobel et al (2007), which is in current use for the 454-platform, is functionally limited to a spatial distance of no more than a few kilo-bases as well as adopting a so termed "out-side-in" topology depicting the reversed orientation of the original termini of the target DNA. The present invention provides method to produce markers of 45- to 50-kb separation distance, whilst retaining an "out-side-out" topology whereby the terminal sequences of the target DNA remain in the same relative orientation. Despite the absence of both template strands on the 454-flow cell, the 500-base read length of the current GS FLX Titanium instrument is sufficient for direct sequence determination of a GVT-pair generated by cleavage of target DNA with frequent cutting FspB I or Csp6 I type II restriction endonucleases from a single read from one template strand.

Cosmid vector pSLGVT-36 enable the production of GVT-pairs of 45- to 50-kb spatial separation in an "out-side-out" topology on the 454 platform. Precise marker spacing of 45- to 50-kb provides economical physical coverage of a genome to identify fine-scale-variations and to span repetitive regions to facilitate the creation of genomic scaffold for de novo genomic sequencing and for mapping fine-scale genomic variations. Sixty thousand GVT-pairs of 50-kb spatial separation represent one-fold-physical coverage of a human-size genome. The current capacity of 454-instrument offers could provide a 20-fold physical coverage of the human genome at 50-kb resolution in a single run, which is a substantial improvement in terms of economy and depth of physical coverage over the Fosmid-paired-end mapping method of Tuzun et al (2005).

Cosmid vector, pSLGVT-36, is a 2.6-kb vector comprising a Kanamycin selection marker, a low copy number P15A origin of replication for stable propagation of genomic DNA, and a COS site for lambda phage packaging. Cleavage sites on the vector for restriction endonucleases FspB I and Csp6 I were eliminated by site-directed mutagenesis, enabling these enzymes to produce GVTs and subsequent GVT-pairs from a target DNA insert in accordance to the methods of this invention. The vector's target DNA cloning site is flanked by a pair of Roche Diagnostics' "Adaptor-A" and "Adaptor-B" sequences to enable recovery of the created GVT-pairs by PCR using 454-Adaptor-A and -B primers. The recovered amplified GVT-pairs, flanked by Adaptors-A and -B sequences, are amplified by emulsion PCR to produce template for 454-sequencing.

Operationally, target DNA for the generation of 45- to 50-kb GVT-pairs for the 454-platform is sheared to a fragment size of 40- to 60-kb and the ends repaired with $T_4$-DNA polymerase. The repaired target DNA is ligated to pSLGVT-36 vector. Ligation of cosmid vector to target DNA is accomplished at equal molar ratio of linearized vector to target DNA insert and at a high-DNA concentration (typically 2- to 3-ug or more per ul total nucleic acids) to drive the production of long concatemers comprising alternating vector and target DNA fragments. The ligated product is packaged into phage particles using commercially available packaging extracts (Stratagene, LA Jolla, Calif.). The propagation of methylated target DNA such as genomic DNA requires host cell strains with inactive mcr and mrr alleles. Suitable host strains include: 10G (Lucigen, Middleton, Wis.); XL1-Blue MR and XL2-Blue MRF' (Stratagene, La Jolla, Calif.). Infected cells are plated onto 10-cm diameter agar plates at a density of ~20,000 to 50,000 colonies per plate under Kanamycin selection to yield a primary cosmid library comprising target DNA inserts of average 45- to 50-kb flanked on one side by 454-Adaptor-A and the other side by 454-Adaptor-B. An alternative method is to grow the infected cells in liquid culture while exercising care not to overgrow cells to encourage undesirable clonal selection. The total number of clones under culture should reflect the number of GVT-pairs required by the study design. Cells are harvested and the cosmid isolated for GVT-production. Purified cosmid DNA bearing target DNA is digested to completion with FspB I or Csp6 I. Digested products are passed through a CHROMASPIN 1000 (Clontech, Mountain View, Calif.) column to remove the bulk of the digested target DNA insert. The flow through material is electrophorsed on an agarose gel. DNA fragments of approximate 2.6- to 3-kb, corresponding to the intact linear cosmid vectors with two attached GVTs corresponding to the termini of the target DNA are recovered from the gel. The recovered material is diluted to less than 25 ng/ul for intra-molecular ligation to create the GVT-pair. Ligation junction of the newly juxtaposed GVTs is demarcated by the recreation of the restriction endonuclease site of the enzyme used to generate the GVT. The recreated restriction site, which is now unique on the molecule, sets the boundary of the GVTs within the GVT-pairs in the subsequent data analysis. The resulting GVT-pair is recovered from the vector backbone by DNA amplification using Adaptor A and B primers. Amplified GVT-pairs flanked by 454-Adaptors are amplified directly on beads by emulsion PCR for 454-sequencing.

It is considered within the scope and the principle of the present invention to produce GVTs and GVT-pairs of other spatial separation with or without the use of in vitro virus packaging, as well as with or without a propagation step through a host cell. In the latter case, target DNA inserts bearing specific 454-Adaptors at each end are cloned into a suitable DNA backbone bearing a COS site and are then packaged into phage heads using commercially available packaging extracts (Stratagene, La Jolla, Calif.). The DNA backbone can be labeled with a purification moiety, such as biotin, to facilitate affinity purification of the desired DNA product. Unpackaged DNA is degraded with nucleases where upon the protected packaged DNA is purified by phenol extraction. The target DNA in the resulting circular DNA molecule is cleaved with the appropriate restriction endonuclease to produce a linear molecule comprising the DNA backbone with attached GVTs. The desired linear DNA is purified by affinity chromatography. The exposed GVT ends are recircularized by intra-molecular ligation with DNA ligase to produce the GVT-pair as well as to seal DNA at the COS site to yield a stable circular molecule. GVT-pairs are recovered by PCR from the ligation mixture using Adaptor A- and B-primers for 454 sequencing.

Production of GVT-Pairs of 45- to 50-kb Spatial Separation on the 454-Platform Outside-In Topology When combined with phage packaging, it is also considered within the scope and the principle of the present invention to produce GVT-pairs with an "out-side-in" topology as it relates to an approach described by Berka et al (2006) (U.S. Patent Application 2006/0292611) and Kobel et al (2007), where the terminal markers adopts an inverted orientation.

Cosmid vector pSLGVT-38 or its derivatives are used to produce GVT-pairs of 45- to 50-kb spacing with a so termed "out-side-in" topology from a target DNA population for DNA sequencing on the 454-platform. pSLGVT-38 is a 2.6-kb vector comprising a Kanamycin selection marker, a low copy number P15A origin of replication for stable propagation of genomic DNA, and a COS site for lambda phage packaging. Cleavage sites on the vector for restriction endonucleases FspB I and Csp6 I were eliminated by site-directed mutagenesis, enabling these enzymes to produce GVTs and a subsequent GVT-pair from any target DNA insert in accordance with the methods of this invention. The vector's target DNA cloning site is flanked by a pair of Roche Diagnostics' 454-"Internal Adaptor-A" and 454- "Internal Adaptor-B" sequences to enable recovery of the created GVT-pairs by PCR using 454-Internal Adaptor-A and -B primers. pSLGVT-38 also contain matched pairs of eight-base rare cutting restriction sites on each side of 454-Internal Adaptors-A and -B enabling one to recover the GVT-pair and flanking Internal Adaptor sequences by enzymatic digestion.

Operationally, target DNA for the generation of 45- to 50-kb GVT-pairs for the 454-platform is sheared to a fragment size of 40- to 55-kb and the ends repaired with $T_4$-DNA polymerase. The repaired target DNA is ligated to pSLGVT-38 vector. Ligation of cosmid vector to target DNA is accomplished at equal molar ratio of linearized vector to target DNA insert and at a high-DNA concentration (typically 2- to 3-ug or more per ul total nucleic acids) to drive the production of long concatemers comprising alternating vector and target DNA fragments. The ligated product is packaged into phage particles using commercially available packaging extracts (Stratagene, LA Jolla, Calif.). The propagation of methylated target DNA such as genomic DNA requires host cell strains with inactive mcr and mrr alleles. Suitable host strains include: 10G (Lucigen, Middleton, Wis.); XL1-Blue MR and XL2Blue MRF' (Stratagene, La Jolla, Calif.). Infected cells are plated onto 10-cm diameter agar plates at a density of 20,000 to 50,000 colonies per plate under Kanamycin selection to yield a primary cosmid library comprising target DNA inserts of average 45- to 50-kb flanked on one side by 454-Internal Adaptor-A and the other side by 454-Internal Adaptor-B. An alternative method is to grow the infected cells in liquid culture while exercising care not to overgrow cells to encourage undesirable clonal selection. The total number of clones under culture should reflect the number of GVT-pairs required by the study design. Cells are harvested and the cosmid isolated for GVT-production. Purified cosmid DNA bearing target DNA is digested to completion with either FspB I or Csp6 I. Digested products are passed through a CHROMASPIN 1000 (Clontech, Mountain View, Calif.) column to remove the bulk of the digested target DNA insert. The flow through material is electrophorsed on an agrose gel. DNA fragments of approximate 2.6- to 3-kb, corresponding to the intact linear cosmid vectors with two attached GVTs corresponding to the termini of the target DNA are recovered from the gel. The recovered material is diluted to less than 25 ng/ul for intra-molecular ligation to create the GVT-pair. Ligation junction of the newly juxtaposed GVTs is demarcated by the recreation of the restriction endonuclease site of the enzyme used to generate the GVTs. The recreated restriction site, which is now unique on the molecule, sets the boundary of the GVTs within the GVT-pairs in the subsequent data analysis. The resulting GVT-pair is recovered from the vector backbone by DNA amplification using 454-Internal Adaptor-A and -B primers. The resulting products are recircularized via the Internal Adaptors and are then digested with the type II restriction endonuclease used to create the GVT (either FspB I or Csp6 I). The linear molecule now comprises a GVT-pair with an "out-side-in" topology where the original termini of the target DNA insert are now inverted in relative orientation with a GVT on each side of newly ligated Internal Adaptors. The so produced linear molecular is ligated with 454-Adaptors-A and -B for sequencing on the 454-platform.

Production of GVT-Pairs of 45- to 50-kb Spatial Separation on the Solid Platform Applied Biosystems' SOLiD platform for massively parallel DNA sequencing is based on sequential cycles of DNA ligation. By this approach, immobilized DNA templates are clonally amplified on beads, which are plated at high density onto the surface of a glass flow-cell where sequencing occurs. Sequence determination is accomplished by successive cycles of ligation of short defined labeled probes onto a series of primers hybridized to the immobilized template. The current SOLiD instrument run comprises more than 200 million individual 50-base reads.

While the SOLiD platform offers the greatest number of base calls per instrument run, the platform is limited by its short read length and not having both template strands available for sequencing in the flow cell. Consequently, the SOLiD platform's "mate-pair" system for pair-end-reads relies on the use of EcoP 15 I digestion to create a pair of short DNA tags of 25-base each representing the termini of a target DNA and the adoption of an "out-side-in" topology similar to the method of Berka et al (2006) (U.S. Patent Application 2006/0292611) and Kobel et al (2007) in order to create an internal DNA sequencing primer binding site to sequence the other member of the tag pair. The spatial distance between tags offered by the current "mate-pair" system is only a few kilo-base and would stand to benefit from the 45- to 50-kb spatial distance of the GVT-pair of the present invention.

When combined with phage packaging, it is considered within the scope and the principle of the present invention to produce GVT-pairs with an "out-side-in" topology as it relates to the approach described by Berka et al (2006) (U.S. Patent Application 2006/0292611) and Kobel et al (2007), where the terminal markers adopt an inverted orientation. In addition, the present invention offers the advantage to produce GVTs of average lengths of 100- to 200-base, a considerable improvement over the 25-base tags produced by the present mate-pair system using EcoP15 I digestion.

Cosmid vector pSLGVT-37 or its derivatives are used to produce GVT-pairs of 45- to 50-kb spacing with a so termed "out-side-in" topology from a target DNA population for DNA sequencing on the SOLiD platform. pSLGVT-37 is a 2.6-kb vector comprising a Kanamycin selection marker, a low copy number P15A origin of replication for stable propagation of genomic DNA, and a COS site for lambda phage packaging. Cleavage sites on the vector for restriction endonucleases FspB I and Csp6 I were eliminated by site-directed mutagenesis, enabling these enzymes to produce GVTs and a subsequent GVT-pair from any target DNA insert in accordance to the methods of this invention. The vector's target DNA cloning site is flanked by a pair of Applied Biosystems' (ABI) "Internal Adaptor-A" and "Internal Adaptor-B" sequences to enable recovery of the created GVT-pairs by PCR using ABI-Internal Adaptor-A and -B primers. pSLGVT-37 also contains matched pairs of eight-base rare cutting restriction sites on each side of ABI-Internal Adaptors-A and -B enabling the recovery of GVT-pairs and flanking Internal Adaptor sequences by enzymatic digestion, if required.

Operationally, target DNA for the generation of 45- to 50-kb GVT-pairs for the ABI SOLiD platform is sheared to a fragment size between 40- to 55-kb and the ends repaired with $T_4$-DNA polymerase. The repaired target DNA is ligated to pSLGVT-37 vector. Ligation of cosmid vector to target DNA is accomplished at equal molar ratio of linearized vector to target DNA insert and at a high-DNA concentration (typically 2- to 3-ug or more per ul total nucleic acids) to drive the production of long concatemers comprising alternating vector and target DNA fragments. The ligated product is packaged into phage particles using commercially available packaging extracts (Stratagene, LA Jolla, Calif.). The propagation of methylated target DNA such as genomic DNA requires host cell strains with inactive mcr and mrr alleles. Suitable host strains include: 10G (Lucigen, Middleton, Wis.); XL1-Blue MR and XL2Blue MRF' (Stratagene, La Jolla, Calif.). Infected cells are plated onto 10-cm diameter agar plates at a density of ~20,000 to 50,000 colonies per plate under Kanamycin selection to yield a primary cosmid library comprising target DNA inserts of average 45- to 50-kb flanked on one side by ABI-Internal Adaptor-A and the other side by ABI-Internal Adaptor-B. An alternative method is to grow the infected cells in liquid culture while exercising care not to overgrow cells to encourage undesirable clonal selection. The total number of clones under culture should reflect the number of GVT-pairs required by the study design. Cells are harvested and the cosmid isolated for GVT-production. Purified cosmid DNA bearing target DNA is digested to completion with either FspB I or Csp6 I. Digested products are passed through a CHROMASPIN 1000 (Clontech, Mountain View, Calif.) column to remove the bulk of the digested target DNA insert. The flow through material is electrophorsed on an agrose gel. DNA fragments of approximate 2.6- to 3-kb, corresponding to the intact linear cosmid vectors with two attached GVTs corresponding to the termini of the target DNA are recovered from the gel. The recovered material is diluted to less than 25 ng/ul for intra-molecular ligation to create the GVT-pair. Ligation junction of the newly juxtaposed GVTs is demarcated by the recreation of the restriction endonuclease site of the enzyme used to generate the GVT. The recreated restriction site, which is now unique on the molecule, sets the boundary of the GVTs within the GVT-pairs in the subsequent data analysis. The resulting GVT-pair is recovered from the vector backbone by DNA amplification using ABI-Internal Adaptor-A and -B primers. The resulting products are recircularized via the Internal Adaptors and are then digested with the type II restriction endonuclease used to create the GVTs (either FspB I or Csp6 I). The linear molecule comprises a GVT-pair with an "out-side-in" topology where the original termini of the target DNA insert are now inverted in orientation with a GVT on each side of newly ligated Internal Adaptors. The so produced linear molecular is ligated with ABI-Adaptors-P1 and P2 for sequencing on the ABI's SOLiD mate-pair platform.

In a preferred embodiment, the present invention identifies fine-structural-variations within a target genome through the creation of a plurality of GVT-pairs of unique genomic positional identifiers of defined spatial distance and orientations. The plurality of GVT-pairs collectively represent the genomic profile of the subject, which, when compared with a reference sequence or to similarly produced genomic profiles of other target genomes, denote the presence of fine-structural-differences between nucleic acid populations. Genomic fine-structural-variations detectable by the present invention include: deletion and insertions, duplication, inversions, translocation and other chromosomal rearrangements. The present invention offers means to identify these genomic features at a user-defined resolution level dictated by the experimental design.

The present invention offers the creation of GVTs of several hundred bases average length, that is limited only by the effective read length of the DNA sequencing platform. Assuming uniform abundance and random distributions of the four bases, the current 76-base read length of the SOLEXA platform would predict that sequences of this length would occur by chance on average once every $4^{76}$ base pairs, and should represent a unique sequence identifier in the human and other complex genomes. However, unequal representation of the fours bases and the presence of extensive regions of repetitive DNA present in many complex genomes result in the inability to assign a significant portion of short DNA tags of this size to unique genomic positions in practice. Unambiguous assignment of a GVT of a given length to the genome improves with linkage to a second GVT along with knowledge of their separation distance. For example, a GVT-pair comprising two spatially linked 76-bp GVTs produced from a size-fractionated target DNA population is effectively a 152-bp sequence tag. Despite the longer effective tag length, it still might not be possible to assign a number of GVTs or GVT-pairs to unique genomic positions, such as those GVT-pairs that reside completely within very long repeated regions of the genome. Nevertheless, the present invention offers a substantial improvement in the generation of mappable pair-end-reads. Regions that are resistant to analysis by the present invention are expected to be very small, largely due to the ability of the present invention to produce GVT-pairs of 40- to 50-kb or more separation distance, which would span most localized regions of repetitive DNA.

The common framework sequence present on each GVT-pair monomer allows unambiguous extraction of GVT-pair sequences from the high-throughput sequence data. Discordance between map positions of GVT-pairs to one or more reference sequences is revealed by alignment using MEGA-BLAST (Zhang et al, 2000) or similar computer programs. Discordance of the GVT-pair separation distance or orientation with the reference over a threshold level signals the presence of a structural difference between target and reference DNA. The threshold level is set by the experimental design, two standard deviations over the mean GVT separation distance being a reasonable default value. Deletions in the target DNA may be defined by two or more GVT-pairs spanning greater than two standard variations from the mean separation distance when compared to the reference sequence. Accordingly, insertions in the target DNA may be defined as sites where two or more GVT-pairs spanning less than two standard variations from the mean separation when compared to the reference sequence. Inversions in target DNA are defined as sites where two or more GVT-pairs have inconsistent orientation of their GVTs when compared to the reference sequence. Discordant GVT-pairs are manually curated and assessed before proceeding to validation by PCR, Southern blot hybridization analysis, or by insert isolation and sequencing.

Target genomic nucleic acids used by the invention can be derived from any source including: genomic DNA of eukaryotic, prokaryotic organisms, microbes, plastids, and viruses. Target genomic nucleic acids can also be derived from RNA genomes of organisms such as the RNA viruses through a reverse-transcription process to convert RNA to DNA. The choice of target nucleic acids for investigation may be influenced by prior knowledge of association of a particular chromosome or chromosome region with certain disease conditions described in the scientific literature. The present invention can utilize target DNA from isolated chromosomes or chromosome regions. The present invention can be used in broad, whole genome-wide scans of patient cohorts at a range of resolutions to suit the study design. Methods for the purification of chromosome, chromosome segments, and genomic DNA and RNA are known in the art. Also known in the art are methods to amplify nucleic acids by PCR or by other means to produce target DNA for analysis by the present invention.

Methods to cleave target DNA and to fractionate target DNA to a desired size for setting the spatial distance between GVTs of a GVT-pair are described herein above. Hydrodynamic shearing, adaptive focused acoustics, or partial enzymatic digestion of DNA with frequent cutting enzymes can be used to produce a population of DNA fragments with a high degree of overlapping fragments for maximal coverage of every region of the target DNA. Alternatively, target DNA can be digested to completion with several restriction endonucleases in separate cleavage reactions and then size-fractioned to desired size classes for GVT-pair production. GVT-pairs produced from size-selected target DNA prepared from completion digestion with a single restriction endonuclease are non-overlapping and would cover only a portion of the target DNA complexity. Size-selected DNA fragments from complete enzymatic digestions with one or more other restriction endonucleases can be used to provide overlaps in sequence coverage. Experimental physical parameters such as the method of DNA fragmentation, GVT separation distance and combinations thereof to cover a genome of a given complexity, base composition, or distribution of repetitive elements can be modeled computationally by workers that are skilled in the art to derive an optimal study design. Enzymes such Bam H I, Hind III, Pst I, Spe I, and Xba I are insensitive to CpG methylation and would expect to cleave mammalian genomic DNA at every site to produce GVT-pairs that accurately represent pairs of adjacent recognition sites for those enzymes. Other suitable enzymes that are insensitive to the effect of CpG methylation, overlapping CpG methylation, or other kinds of DNA modifications that may influence nucleic acid analysis by the present invention have been described in the literature (McClelland et al, 1994; Geier et al, 1979; Kan et al, 1979; Hattman et al, 1978; Buryanov et al, 1978; May et al, 1975) and by major vendors of restriction endonucleases (Fermentas, Hanover, Md.; New England Biolabs, Ispwich, Mass.). In certain embodiments, the use of enzymes whose cleavage of target DNA is sensitive to DNA modifications may be used to demarcate sites of epigenomic modifications in the target DNA. For example, the present invention can identify sites of DNA methylation, which are known to regulate gene expression. For such an application, target DNA is digested to completion with a methylation sensitive restriction enzyme and GVT-pairs produced from the digested DNA. Sites of methylation are identified by discordance of the resulting GVT-pairs when compared to adjacent restriction sites on the reference sequence.

Discordant GVT-pairs are first manually curated before proceeding to a series of hierarchical filters for validation. In cases where the discordant GVT-pairs are produced from size-selected DNA derived from complete restriction endonuclease digestion, Southern blot analysis of target DNA and reference DNA digested with the same restriction endonuclease could be used to validate differences in marker distance between target and reference DNA. The GVTs are of sufficient length for use as specific PCR primers to isolate the intervening genomic sequence for shotgun sequencing to determine the precise nature of the structural variation.

It is generally accepted the study of structural variations will shed new light on complex diseases, such as obesity and diabetes, whose development is triggered by the interactions of genes, genetic elements, and the environment. The choice of nucleic acids for analysis by the present invention may be influenced by prior knowledge of association of a particular chromosome or chromosome region with certain disease conditions described in the scientific literature. The present invention can target DNA from isolated chromosomes or chromosome regions or tissue samples at high resolution. Alternatively, the present invention can be used in broad, whole genome-wide scans of patient cohorts at a range of resolutions to suit the study design. The technique of fosmid paired-end mapping (Tuzun et al, 2005) requires more than two million conventional Sanger dideoxy-based sequencing reads (Sanger, 1977) to analyze an individual at a moderate level of resolution and coverage, thereby limiting its use to scan large populations for association studies to find biomarkers that are diagnostic or prognostic to disease outcome as well as potential drug targets for medical intervention. The present invention offers a solution to these limitations, and as such it has the potential to create new medical diagnostics and to aid drug discovery.

In another preferred embodiment, fine-structural-variations identified by the present invention are used to design oligonucleotide array assays, microarray assays, PCR-based assays, and other diagnostic assays in the art to detect differences between nucleic acid populations. Present microarrays and oligonucleotide arrays are efficient platforms for detection of nucleic acid copy number alterations and single or small nucleotide polymorphisms, but are not suited to detect other genomic changes that may contribute to or are causal of disease. The identified products of the present invention enable the design of oligonucleotide and microarray assays or other diagnostic assays in the art to screen translocation, insertion, deletion, and inversion junctions that demarcate fine-structural-variations identified by the present invention. These assays can then be used to screen general population and large patient cohorts to determine the role of fine-structural-variations in complex diseases such as obesity, diabetes, and many cancers, whose development is triggered by the interactions of multiple genetic and environmental factors. Other uses for these assays include but are not limited to the diagnosis or the differentiation between closely related species, strains, races, or biotypes of organisms with utilities in the fields of medical diagnostics, phylogenetics and industrial microbiology.

In another preferred embodiment, the present invention is used to create high-resolution genomic maps to aid de novo genomic assembly from "shotgun DNA sequencing". Shotgun sequencing was introduced by Sanger et al (1977), in which a genomic DNA is fragmented randomly into small fragments for individual sequencing, after which the sequences are assembled to construct the sequence of the genome. Shotgun approach is challenging for complex genomes, where false overlaps may occur owing to repeated sequences. Two approaches are used to deal with complex genomes. The hierarchical approach involves generating overlapping sets of intermediate-size clones, such as BAC, selecting a tiling path of these clones, and then subjecting each clone to shotgun sequencing. In this way, a large genome is decomposed into smaller more "manageable genomes". The second approach is termed "whole-genome-shotgun" (WGS) where the entire genome sequence is generated directly from short overlapping sequence reads using computational methods in one fell swoop. Two advances made WGS feasible: (1) Edward et al (1990) introduced the use of paired-end reads by sequencing the ends of inserts of a known approximate size to provide linkage information of distance constraints between the two sequence reads; and (2) the development of assembly algorithms capable of using pair-end sequence information (Huang et al, 2006; Warren et al, 2006; Pop et al, 2004; Havlak et al, 2004; Jaffe et al, 2003; Mullikin and Ning, 2003; Huang et al, 2003; Batzoglou et al, 2002; Pevzner and Tang, 2001; Myers et al, 2000). Clone length constraints are supplied to the WGS assembly programs as permissible distances between pairs of sequence reads. This information is crucial for resolving repeated sequences by permitting the construction of scaffolds, which link, order and orientate sequence contigs for increasing the long-range contiguity of the resulting sequence assemblies. Plasmid pair-end-reads of Edwards et al (1990) were later supplemented by BAC pair-end-reads to build higher order scaffolds (Warren et al, 2006; Zhao, 2000; Mahairas et al, 1999). However despite the extensive use of pair-end-reads, most draft genome sequences contain thousands of miss-assemblies (Salzberg and Yorke, 2005). Assembly errors stem from an amalgam of problems from deficiencies in software, difficult repeated regions in the genome, the diploid nature most large genomes, as well as scaffolds of insufficient resolution and coverage. Insufficient scaffold resolution stems to a great extent from the imprecise distances of pair-end-reads derived from plasmid or BAC inserts, since it is impractical to size every single clone sequenced using current laboratory protocols. Moreover, the constructed scaffolds are not optimized for the required number of elements and spacing to achieve a necessary spatial resolution. The present invention provides methods to produce high-resolution scaffolds to enable genome assembly, in particular de novo assembly of uncharacterized genomes where there is often no prior structural information available. Specifically, the present invention provides improved methods to produce GVTs, which in one embodiment represents an improved functional equivalent to the classical pair-end-reads of Edward et al (1990), Zhao (2000), and Tuzun (2005). In contrast to the classical pair-end-reads, GVT-pairs have the capability to tailor spacing accurately to any desired configuration and most importantly, the ability to mark adjacent restriction endonuclease sites in the genome to offer an independent corroboration of the accuracy of the resulting genomic assembly. GVT-pairs are amenable to high-throughput DNA sequencing on conventional Sanger-based dideoxy-based sequencing chemistry or the new generation 454—(Roche Diagnostics, Indianapolis, Ind.), SOLEXA (Illumina, San Diego, Calif.), or SOLiD (Applied BioSystems, Foster City, Calif.) instruments to provide a complete cost-effective coverage of the target genomes. Hence, the present invention provides a comprehensive set of unique genetic markers of defined separation distance or of adjacent restriction endonuclease sites to facilitate whole genome shotgun sequencing efforts.

It is expected that a number of GVT-pairs produced by the present invention that are discordant to the present build of the Human Genome Assembly (Build 36, April 2006) may not actually represent fine-structural variation in the target DNA, but rather reflect errors or gaps in the current Human Genome Assembly. Further compounding the problem is that the current Genome Assembly is derived from DNA of pooled multiple donors. Reference sequences derived from a large number of single individuals that are representative of the range of human diversity are needed to move the genomics field forward. The utility offered by the present invention provides the means to do so economically.

In another preferred embodiment, the present invention is used to create high-resolution genomic maps to facilitate phylogenetic studies and for determining the genetic and functional relationship between closely related organisms. An aspect of the invention especially suited for this application makes use of GVT-pairs produced firm target DNA digested to completion with one or more restriction endonucleases alone or in useful combination for GVT-pair production without a DNA size-fractionation step. Essentially, the so produced GVT-pairs constitute a genomic profile comprising pairs of positional markers that demarcate adjacent restriction endonuclease sites along the length of the target DNA. The identity of the GVT-pairs and their relative abundance can be used to create high-resolution genomic profiles that can be used to identify, differentiate, and quantify the genome of origin within a complex medical or environmental DNA isolate. The produced GVT-pairs also have utility in the area of industrial microbiology for identifying genomic differences causal to desirable traits, such as favorable growth rate and the production of useful secondary metabolites and recombinant proteins in closely related strains, biotypes, or race of genetically modified organisms. As such, the present invention can aid strain improvement in the industrial production from microbial or mammalian host cells. High resolution genomic maps produced by the present invention also offer a low cost and effective means to survey the nucleic acids of closely related pathogens to identify regions of variations to target detailed sequence analysis to identify pathogenic determinants that can be used for diagnosis and as drug targets for medical intervention.

In another preferred embodiment, the present invention can be used for genetic dissection of phenotype diversity in farm animals and agricultural crops to facilitate marker-assisted breeding. Farm animals are of a particular interest for identifying the complex genetic elements that contribute to the control of growth, energy metabolism, development, body composition, reproduction, and behavior, as well as other traits sought by classical breeding. For a review see Andersson (2001). Most agricultural traits of interest are multifactorial and are often controlled by an unknown number of quantitative trait loci (QTL). Micro-satellite maps for genomic scans have been developed for the major farm animals. Association studies using these markers and the candidate gene approach are the two major strategies used for the identification of QTLs. The cloning of QTLs is challenging since the relationship between genotype and phenotype is considerably more complex than for the monogenic traits. However, it is possible to determine the QTL indirectly by progeny testing where the segregation of the QTLs is deduced using data from genetic markers and phenotypic variations among the progeny. At present, the molecular basis for most QTLs is as yet unknown. QTL mapping in Drosophila suggests that QTLs are often associated with sequence variations in the noncoding regions (MacKay, 2001). As in man, it is expected that fine-structural-variations in the genomes of farm animals and crop plants will likely play an important role in phenotypic expression and interaction of the genome with the environment. The present invention provides the means to tabulate the comprehensive range of genomic structural diversity in farm animals and crop plants at low cost. The tabulated information would then enable the creation of oligonucleotide microarrays and other diagnostic platforms for use in association and linkage studies to identify and characterize the actual QTLs leading to marker-assisted breeding.

As the major pollinator, bees play a critical role in agriculture and in many parts of the world. Apiculture is another area that stands to benefit from the present invention. The honeybee is an economically important species suited to use of genetic technology in breed development. Bees have a short generation time and produce large number of progeny. Lines are also readily propagated by artificial insemination. Bee strains exhibit broad phenotypic variations in productivity, disease resistance, and behavioral traits, many of which are under complex genetically control. Important behavioral traits under genetic control include: aggression as exemplified by many African strains, foraging habits, honey yield and the so termed "hygienic" behavior. The "hygienic" trait is regulated by at least seven as yet undefined genetic loci, which in sum result in the cleaning behavior by the hive members to rid dead or diseased broods as a primary defense against fungal and mite infestation, two major economic bee pathogens. A primary goal is to develop reliable diagnostic molecular markers that could be used in marker-assisted breeding to identify the desired progeny strains quickly and efficiently without the need for complicated and time consuming breeding experiments and field assays. Genetic maps and a reference sequence of the 200 mega-base size genome of *Apis mellifera* strain DH4 (Weinstock, 2006) is available for use by the present invention to provide efficient and low cost methods to survey genomes of multiple bee strains for fine-structural-variations at high resolution to correlate desired phenotype to genotype. The ability to survey multiple strains cost effectively is a key advantage offered by the present invention.

In another preferred embodiment, the present invention can be used to identify genetic causes underlying neurological disorders and traits. It is generally believed that at least a component of many neurological disorders such as autism, bipolar disorder, and schizophrenia have a complex non-Mendelian genetic component (Craddock and Jones, 2001; Owen and Craddock, 1996; Holzman and Matthysse, 1990). Complementing linkage and association studies in current use to identify the genomic components, the present invention provides means to assess the contributory role of genomic fine-structural-variations in neurological disorders and may lead to new methods for diagnosis, prognosis and patient management.

In another preferred embodiment, the present invention can be used to identify genetic causes underlying cancer and thereby create means for diagnosis, prognosis, and therapeutic intervention. Virtually all cancers are due to abnormalities in DNA sequence, either inherited or acquired through somatic mutations during life. The prevailing tenet of oncogenesis is that together with environmental factors, accumulating genetic and somatic DNA mutations alter gene expression or gene functions past a critical functional threshold that allows clonal expansion, cellular invasion of surrounding tissues, and the initiation of metastasis. One in three people in the Western World will develop cancer and one in five will die directly from the disease, making cancer the most common of the genetic diseases. The field historically began with the identification of potent onco- or tumor suppressor genes where a simple loss or gain of function due to a small number of nucleotide changes to a locus was the major contributory factor to cancer. The field has since expanded to gene dosage where duplication or deletion of DNA segments resulting in alteration of gene copy number is the presumed cause of oncogenesis. Array CGH has been particularly useful for the detection of alteration in DNA copy number and the loss of heterozygosity in cancer cell lines and primary tumors. A comprehensive review of copy number analysis in cancer and a catalogue of somatic mutation in cancer and references therein can be found in under "The Cancer Genome Project" of the Sanger Institute (www.sanger.ac.uk/genetics/CGP/).

Most recently, the important role of genomic fine-structural-variations in oncogenesis has been recognized. During the course of oncogenesis, the tumor genome accumulates a large number of rearrangements, including amplifications, deletions, translocations, inversions, and the like, many of which contribute directly to tumor progression (Gray and Collins, 2000). Volik et al (2006) made use of a variation of fosmid paired-end mapping to detect all changes in genomic architecture of a progressing tumor, in particular translocations and inversion events that are not detectable by array CGH. Their attempt to dissect the breast cancer genome was most informative but was acknowledged by the investigators to be limited by the expense and resources required to obtain end-terminal sequences of the large number of BAC clones for each sample. The present invention offers low cost, high-resolution methods to overcome these deficiencies and to identify genomic fine-structural-variations not amendable to detection by array CGH. The present invention has sufficiently low cost when used in conjunction with the next generation DNA sequencers to enable use in broad surveys of cancer patient cohorts and for use to track the accumulation of genomic changes in tumor progression in individual patients. The ability to track genomic changes during tumor progression would have profound predictive value in clinical outcome, providing significant improvements in patient management.

It is to be understood that various other modifications will be apparent to and can readily be made by those that are skilled in the art, given the disclosure herein, without departing from the scope and spirit of this invention.

References

The following as well as all other articles, patents, and published applications mentioned throughout this application are incorporated by reference:

Albertson DG and Pinkel D, 2003. Genomic microarrays in human genetic disease and cancer. *Hum Mol Gen* 12 *Spec No* 2: *R*145-*R*152.

Albertson DG et al, 2000. Quantitative mapping of amplicon structure by array CGH identifies CYP24 as a candidate oncogene. *Nat Genet* 25: 144-146.

Andersson L, 2001. Genetic dissection of phenotypic diversity in farm animals. *Nat Rev* 2: 130-138.

Bailey AB et al, 2002. Recent segmental duplications in the human genome. *Science* 297: 1003-1007.

Batzoglou S et al, 2002. ARACHNE: A whole-genome shotgun assembler. *Genome Res* 12: 177-189.

Berka J et al, 2006. Paired end sequencing. U.S. Patent Application No US 2006/0292611.

Bignell GR et al, 2004. High-resolution analysis of DNA copy number using oligonucleotide microarrays. *Genome Res* 14: 287-295.

Bolivar F et al, 1977. Construction and characterization of new cloning vehicles. II multipurpose system. *Gene* 2: 95-113.

Brennan C et al, 2004. High-resolution global profiling of genomic alterations with long oligonucleotide microarray. *Cancer Res* 64: 4744-4748.

Bujnicki JM, 2001. Understanding the evolution of restriction-modification systems: Clues from sequence and structure comparisons. *Acta Biochimica Polonica* 48: 935-967.

Buryanov YI et al, 1978. Site specific and chromatographics properties of *E coli* K12 and Eco RII DNA-cytosine methylases. *FEBS Lett* 88: 251-254.

Chang ACY and Cohen SN, 1978. Construction and characterization of amplifiable multicopy DNA cloning vehicles derived from the P15A cryptic miniplasmid. *J Bacteriology* 134: 1141-1156.

Check E, 2005. Patchwork people. *Nature* 437: 1084-1096.

Cheng Z et al, 2005. A genome-wide comparison of recent chimpanzee and human segmental duplications. *Nature* 437: 88-93.

Collins FS et al, 1987. Construction of a general human chromosome-jumping library, with application in cystic fibrosis. *Science* 235: 1046-1049.

Collins FS and Weissman SM, 1984. Directional cloning of DNA fragments at a large distance from an initial probe: A circularization method. *Proc Natl Acad Sci (USA)* 81: 6812-6816.

Craddock N and Jones I, 2001. Molecular genetics of bipolar disorder. *Br J Psychiatry Suppl* 41: S128- S133.

Deininger PL, 1983. Random subcloning of sonicated DNA: Application to shotgun DNA sequence analysis. *Analyt Biochem* 129: 216-223.

Dugaiczyk A et al, 1975. Ligation of Eco RI endonuclease-generated DNA fragments into linear and circular structures. *J Mol Biol* 96: 171-178.

Dunn JL et al, 2002. Genomic signature tags (GSTs): A system for profiling genomics DNA. *Genome Res* 12: 1756-1765.

Edwards A et al, 1990. Automated DNA sequencing of the human HPRT locus. *Genomics* 6: 593-608.

Feng T et al, 2002. Increased efficiency of cloning large DNA fragments using a lower copy number plasmid. *BioTechniques* 32: 992-998.

Feuk L et al, 2006. Structural variation in the human genome. *Nature Rev* 7: 85-97.

Fitzgerald MC et al, 1992. Rapid shotgun cloning utilizing the two base recognition endonuclease *CviJ I*. *Nuc Acid Res* 20: 3753-3762.

Geier GE and Modrich P, 1979. Recognition sequence of the dam methylase of *Escherichia coli*K12 and mode of cleavage of Dpn I endonuclease. *J Biol Chem* 254: 1408-1413.

Gonzalez E et al, 2005. The influence of CCL3L1 gene-containing segmental duplications on HIV-1/AIDS susceptibility. *Science* 307: 1434-1440.

Gray JW and Collins C, 2000. Genome changes and gene expression in human solid tumors. *Carcinogenesis* 21: 443-452.

Grindley NDF and Joyce CM, 1980. Genetic and DNA sequence analysis of the kanamycin resistance transposon Tn903. *Proc Natl Acad Sci (USA)* 77: 7176-7180.

Hamelin C and Yelle J, 1990. Gel and buffer effects on the migration of DNA molecules in agarose. *Appl Theor Electrophor I:* 225-231.

Hattman S et al, 1978. Sequence specificity of the P1 modification methylase (M.Eco P1) and the DNA methylase (*M. Eco* dam) controlled by the *Escherichia coli* dam gene. *J Mol Biol* 126: 367-380.

Havlak P et al, 2004. The atlas genome assembly system. *Genome Res* 14: 721-732.

Hayashi K et al, 1986. Regulation of inter- and intermolecular ligation with T4 DNA ligase in the presence of polyethylene glycol. *Nuc Acids Res* 14: 7617-7630.

Heffron F et al, 1978. *In vitro* mutagenesis of a circular DNA molecule by using synthetic restriction sites. *Proc Natl Acad Sci (USA)* 74: 6012-6016.

Heiskanen MA et al, 2000. Detection of gene amplification by genomic hybridization to cDNA microarrays. *Cancer Res* 60: 799-802.

Holzman PS and Matthysse S, 1990. The genetics of schizophrenia: A review. *Pyschol Sei* 1: 179-286.

Huang J et al, 2004. Whole genome DNA copy number changes by high density oligonucleotides arrays. *Hum Genomics* 1: 287-299.

Huang X et al, 2006. Application of a superword array in genome assembly. *Nuc Acids Res* 34: 201-205.

Huang X et al, 2003. PCAP: A whole-genome assembly program. *Genome Res* 13: 2164-2170.

Inazawa J et al, 2004. Comparative genomic hybridization (CGH)-arrays pave the way for identification of novel cancer-related genes. *Cancer Sci* 95: 559-563.

Jaffe DB et al, 2003. Whole-genome sequence assembly for mammalian genomes: ARACHNE 2. *Genome Res* 13: 91-96.

Kan NC et al, 1979. The nucleotide sequence recognized by the *Escherichia coil* K12 restriction and modification enzymes. *J Mol Biol* 130: 191-209.

Kinzler KW et al, 1995. Method for serial analysis of gene expression. U.S Pat. No 5,695,937 (Issued Dec. 9, 1997).

Korbel JO et al, 2007. Paired-end mapping reveals extensive structure variation in the Human genome. *Science* 318: 420-426.

Kozdroj J and van Elsas JD, 2001. Structural diversity of microorganisms in chemically perturbed soil assessed by molecular and cytochemical approaches. *J Microl Meth* 43: 187-212.

Lok S, 2001. Methods for generating a continuous nucleotide sequence from non-contiguous nucleotide sequences. U.S. Pat. No. 6,730,500 (Issued May. 4, 2004).

Lucito R et al, 2003. Representational oligonucleotide microarray analysis: A high-resolution method to detect genome copy number variation. *Genome Res* 13: 2291-2305.

Mackay TFC, 2001. Quantitative trait loci in *Drosophila*. *Nat Rev Genet* 2:11-20.

Mahairas GG et al, 1999. Sequence-tagged connectors: A sequence approach to mapping and scanning the human genome. *Proc Natl Acad Sci (USA)* 96: 9739-9744.

Mardis ER, 2008. Next-generation DNA sequencing methods. *Annu Rev Genomics Hum Genet* 9: 387-402.

Margulies M et al, 2005. Genome sequencing in microfabricated high-density picolitre reactors. *Nature* 437: 376-380.

Matsumura H et al, 2003. Gene expression analysis of plant host-pathogen interactions by SuperSAGE. *Proc Natl Acad Sci (USA)* 100: 15718-15723.

May MA and Hattman S, 1975. Analysis of bacteriophage deoxyribonucleic acid sequences methylated by host- and R-factor-controlled enzymes. *J Bacteriology* 123: 768-770.

McClelland M et al, 1994. Effect of site-specific modification on restriction endonucleases and DNA modification methyltransferases. *Nuc Acids Res* 22: 3640-3659.

Mead, DA and Godiska R, 2001. Cloning vectors and vector components. U.S. Pat. No. 6,709,861 (Issued Mar, 23, 2004).

Mclgar E and Goldthwait DA, 1968. Deoxyribonucleic acid nucleases: II. The effect of metals on the mechanism of action of deoxyribonuclease 1. *J Biol Chem* 243: 4409-4416.

Morozova O, Marra MA, 2008. Applications of the next-generation sequencing technologies in functional genomics. *Genomics* 92: 255-262.

Mullikin JC and Ning Z, 2003. The PHUSION assembler. *Genome Res* 13: 81-90. Myers EW et al, 2000. A whole-genome assembly of *Drosophila*. *Science* 287: 2196-21204.

Ng P et al, 2005. Gene identification signiture (GIS) analysis for transcriptome characterization and genome annotation. *Nat Meth* 2: 105-111.

Owen MJ and Craddock N, 1996. Modem molecular genetic approaches to complex traits: Implications for psychiatric disorders. *Mol Psychiatry* 1: 21-26.

Pevzner PA and Tang H, 2001. Fragment assembly with double-barreled data. *Bioinformatics* 17*Suppl* 1: S225-S233.

Pheiffer BH and Zimmerman SB, 1983. Polymer-stimulated ligation: Enhanced blunt- or cohesive-end ligation of DNA or deoxyribooligonucleotides by T4 DNA ligase in polymer solutions. *Nuc Acids Res* 11: 7853-7871.

Pinkel D and Albertson DG, 2005. Array comparative genomic hybridization and its application in cancer. *Nat Genet Suppl* 37: S11-S17.

Pinkel D et al, 1998. High resolution analysis of DNA copy number variation using comparative genomic hybridization to microarrays. *Nat Genet* 20: 207-211.

Pinkel D et al, 1997. Comparative genomic hybridization. U.S. Pat. No. 6,159,685 (Issued Dec. 12, 2000).

Pinkel D et al, 1994. Comparative fluorescence hybridization to nucleic acid arrays. U.S. Pat. No. 5,830,645 (Issued Nov. 3, 1998).

Pollack JR et al, 2002. Microarray analysis reveals a major direct role of DNA copy number alternation in the transcriptional program of human breast tumors. *Proc Nail Acad Sci (USA)* 99: 12963-12968.

Pollack JR et al, 1999. Genome-wide analysis of DNA copy-number changes using cDNA microarrays. *Nat Genet* 23: 41-46.

Pop M et al, 2004. Comparative genome assembly. *Briefings in Bioinformatics* 5: 237-248.

Redon R et al, 2006. Global variation in copy number in the human genome. *Nature* 444: 444-454.

Rouillard, J-M et al, 2001. Virtual genome scan: A tool for restriction landmark-based scanning of the human genome. *Genome Res* 11: 1453-1459.

Saha S et al, 2002. Using the transcriptome to annotate the genome. *Nat Biotech* 19: 508-512. Salzberg SL and Yorke JA, 2005. Beware of mis-assembled genomes. *Bioinformatics* 21: 43204321.

Sanger F et al, 1977. DNA sequencing with chain terminating inhibitors. *Proc Natl Acad Sci (USA)* 74: 5463-5467.

Schloter M et al, 2000. Ecology and evolution of bacterial microdiversity. *FEMS Micobiol Rev* 21: 647-660.

Schriefer LA et al, 1990. Low pressure DNA shearing: A method for random DNA sequence analysis. *Nuc Acids Res* 18: 7455.

Sistla S and Rao DN, 2004. S-adenosyl-L-methionine-dependent restriction enzymes. *Crit Rev Biochem Mol Biol* 39:1-19.

Snijders AM et al, 2001. Assembly of microarrays for genome-wide measurement of DNA copy numbers. *Nat Genet* 29: 263-264.

Szybalski W, 1997. Conditionally amplifiable BAC vector. U.S. Pat. No. 5,874,259 (Issued Feb. 23, 1999).

Szybalski E et al, 1991. Class-IIS restriction enzymes-A review. *Gene* 100: 13-26.

Tao Q and Zhang, H-B, 1998. Cloning and stable maintenance of DNA fragments over 300 kb in *Escherichia coli* with conventional plasmid-based vectors. *Nuc Acids Res* 21: 4901-4909.

Tuzun E et al, 2005. Fine-scale structural variation of the human genome. *Nat Genet* 37: 727-732.

Velculescu VE et al, 1995. Serial analysis of gene expression. *Science* 270: 484-487.

Volik S et al, 2006. Decoding the fine-scale structure of a breast cancer genome and transcriptome.*Genome Res* 16: 394-404.

Wang JC and Davidson N, 1966. On the probability of ring closure of lambda DNA.*J Mol Biol* 19: 469-482.

Warren RL et al, 2006. Physical map-assisted whole-genome shotgun sequence assemblies. *Genome Res* 16: 768-775.

Wei C-L et al, 2004. 5' long serial analysis of gene expression (LongSAGE) and 3' LongSAGE for transcriptome characterization and genome annotation. *Proc Natl Acad Sci (USA)* 101: 11701-11706.

Weinstock GM et al, 2006. Insights into social insects from the genome of the honeybee Apis mellifera. *Nature* 443: 931-949.

Wimmer K et al, 2002. Combined restriction landmark genomic scanning and virtual genome scans identify a novel human homeobox gene, ALX3, that is hypermethylated in neuroblastoma. *Genes Chromosomes & Cancer* 33: 285-294.

Zhang Z et al, 2000. A greedy algorithm for aligning DNA sequencing. *I Computational Biol* 7: 203-214.

Zhao S, 2000. Human BAC ends. *Nuc Acids Res* 28: 129-132.

Zimmerman SB and Pheiffer BH, 1983. Macromolecular crowding allows blunt-end ligation by DNA ligases from rat liver or *Escherichia coli*. *Proc Natl Acad Sci (USA)* 80: 5852-5856.

What is claimed is:

1. A method for producing juxtaposing sequence tags (GVTs) for determining a fine-structural-variation of a subject nucleic acid molecule, where two constituent members of a sequence tag pair (GVT-pair) located along the length of a population of target nucleic acid molecules are positional markers of a defined separation distance, and the fine-structural-variation is selected from insertion, deletion, duplication, inversion, translocation, or nucleic acid sequence rearrangement; wherein the method comprises:

fragmenting the subject nucleic acid molecule to form a target DNA insert;

ligating the target DNA insert to a linear DNA backbone at terminal cloning sites of the target DNA insert, leading to the creation of a circular molecule comprising the target DNA insert;

digesting the target DNA insert within the circular molecule using at least one endonuclease cleaving the target DNA insert at a distance from each of the insert's terminal cloning sites and thereby creating a linear molecule comprising two sequence tags (GVTs) comprising the terminal sequences of the target DNA insert, one of the two GVTs attached to each end of the undigested DNA backbone;

recircularizing the linear DNA backbone with the attached GVTs to create a circular DNA molecule thereby creating a GVT-pair comprising two juxtaposed GVTs that are the same relative orientation as the target DNA insert;

isolating the created GVT-pair by nucleic acid amplification from primer sites on the DNA backbone or by digestion with endonuclease at sites that are on the DNA backbone and are flanking the created GVT-pair;

corresponding the GVT-pair to a reference nucleic acid molecule, wherein each GVT corresponds to a segment of the reference nucleic acid molecule;

determining a structural information of interest of the GVT-pair on the subject nucleic acid molecule, wherein the structural information of interest of the GVT-pair on the subject nucleic acid molecule is selected from location of the GVT-pair on the subject nucleic acid molecule, separation distance between the GVT-pair on the subject nucleic acid molecule, or orientation between the GVT-pair on the subject nucleic acid molecule;

determining a corresponding structural information of interest of the segments on the reference nucleic acid molecule, wherein the corresponding structural information of interest of the segments on the reference nucleic acid molecule corresponds to the structural information of interest of the GVT-pair on the subject nucleic acid molecule, and the corresponding structural information of interest of the segments on the reference nucleic acid molecule is selected from location of the segments on the reference nucleic acid molecule, separation distance between the segments on the reference nucleic acid molecule, or orientation between the segments on the reference nucleic acid molecule; and determining whether the subject nucleic acid molecule has a fine-structural-variation as compared to the reference nucleic acid molecule by comparing the structural information of interest of the GVT-pair on the subject nucleic acid molecule with the corresponding structural information of interest of the segments on the reference nucleic acid molecule.

2. The method according to claim 1, wherein the individual GVTs of the isolated GVT-pair are made to adopt an inverted orientation relative to the target DNA insert by the method further comprising:

recircularizing the isolated and created GVT-pair by intramolecular ligation; and digesting the resulting circular molecule with a restriction endonuclease that cleaves the GVT-pair to yield a linear molecule with the GVTs in an inverted orientation.

3. The method according to claim 1, wherein the created GVT-pair comprises two end regions of a target DNA insert having a separation distance that is less than 250-kb in separation, less than 100-kb in separation, less than 50-kb in separation, less than 25-kb in separation, less than 10-kb in separation, less than 5-kb in separation, or less than 2.5-kb in separation.

4. The method according to claim 1, wherein the target DNA insert is either genomic DNA, genomic DNA from isolated chromosomes, DNA isolated from isolated chromosome regions, cDNA, mitochondrial DNA, chloroplast DNA, viral DNA, microbial DNA, plastid DNA, chemically synthesized DNA, DNA product of nucleic acid amplification, or DNA transcribed from RNA.

5. The method according to claim 1, wherein the subject nucleic acid molecule is fragmented randomly to form a target DNA insert by the selected application of mechanical force, partial digestion with one or more nuclease enzymes alone or in combination, or by complete digestion using one or more nuclease enzymes alone or in combination.

6. The method according to claim 1, wherein the subject nucleic acid molecule is fragmented to form a target DNA insert by the use of one or more nucleases that are sensitive to DNA methylation status.

7. The method according to claim 1, wherein the target DNA insert is size fractionated.

8. The method according to claim 1, wherein the target DNA insert is not size fractionated.

9. The method according to claim 1, wherein the target DNA insert is at least 250-kb, at least 100-kb, at least 50-kb, at least 25-kb, at least 10-kb, at least 5-kb, or at least 2.5-kb in length.

10. The method according to claim 1, wherein the restriction endonuclease used to digest the target DNA insert to create the GVTs is a restriction endonuclease that recognizes a four or more base pair recognition sequence.

11. The method according to claim 1, wherein the restriction endonuclease used to digest the target DNA insert to create the GVTs is a type II restriction endonuclease.

12. The method according to claim 11, wherein the type II restriction endonuclease is FspB I, Csp6 I, or any of their isoschizomers or neoschizomers, alone or in combination.

13. The method according to claim 1, wherein the DNA backbone is less than 25-kb in length, less than 10-kb in length, less than 5-kb in length, less than 1-kb in length, less than 500-bp in length, less than 250-bp in length, less than 100-bp in length, or less than 50-bp in length.

14. The method of claim 1, wherein the target DNA insert is first ligated to an adaptor at each end and then the adaptor-ligated target DNA insert is ligated to a DNA backbone.

15. The method according to claim 1, wherein the DNA backbone is assembled from two, three or more DNA segments before, during or after ligating to the target DNA insert.

16. The method according to claim 1, wherein the DNA backbone contains a functional adaptor sequence at one or both termini to facilitate the ligation of the DNA backbone to the target DNA insert.

17. The method according to claim 16, wherein the adaptor is 8-bp to 100-bp in length.

18. The method according to claim 1, wherein the DNA backbone contains one or more sequences that are capable of directing DNA amplification of the created GVT-pair.

19. The method according to claim 18, wherein the DNA backbone contains one or more sequences that are capable of directing DNA amplification of the created GVT-pair on a solid support.

20. The method according to claim 19, wherein the DNA backbone contains one or more sequences that are capable of directing isothermal DNA amplification of the created GVT-pair on a solid support.

21. The method according to claim 1, wherein the adaptor contains one or more sequences that are capable of binding DNA sequencing primers for sequencing the created GVT-pair.

22. The method according to claim 1, wherein the produced GVT-pair is one of a plurality of similarly produced GVT-pairs representative of a library of linked genomic tags from a population of target DNA.

23. The method according to claim 1, wherein the DNA backbone contains one or more nucleotides conjugated to a moiety that is capable of generating a detectable signal that can be read by an instrument or by visual inspection.

24. The method according to claim 1, wherein the DNA backbone contains one or more nucleotides that are conjugated to an affinity purification tag.

25. The method according to claim 24, wherein the affinity purification tag is biotin.

26. The method according to claim 25, comprising the step of isolating nucleic acid fragments by affinity purification with an avidin or streptavidin coated solid support.

27. The method according to claim 1, wherein the DNA backbone is free of palindromic sequences of four bases or greater in length.

28. The method according to claim 1, wherein the DNA backbone is free of recognition and cleavage sites for the type II restriction endonuclease FspB I, Csp6 I, or any of isoschizomers or neoschizomers.

29. The method according to claim 1, wherein methylation of the DNA backbone prevents cleavage by one or more restriction endonucleases.

30. The method according to claim 1, wherein the termini of the DNA backbone are created by digestion with a type IIS restriction endonuclease that produces nucleotide overhangs to facilitate ligation of a target DNA insert bearing the complementary nucleotide overhangs.

31. The method according to claim 30, wherein the termini of the DNA backbone are created by digestion with a type IIS restriction endonuclease that produces a single base 3'- nucleotide overhang at each terminus to facilitate ligation of the target DNA insert bearing a complementary 3'- nucleotide overhang to create a circular molecule.

32. The method according to claim 31, wherein the 3'- single nucleotide extension of the DNA backbone is a thymine base and the complementary 3'- single nucleotide extension on the target DNA insert is an adenine base.

33. The method according to claim 30, wherein the type IIS restriction endonuclease is BciVI or any of its isoschizomers.

34. The method according to claim 30, wherein the DNA backbone is free of the recognition site of the type IIS restriction endonuclease BciVI, or any of its isoschizomers or neoschizomers.

35. The method according to claim 1, wherein the DNA backbone is a DNA vector that is capable of propagation in a cell.

36. The method according to claim 1, wherein the DNA backbone is a bacterial artificial chromosome vector or a yeast artificial chromosome vector.

37. The method according to claim 1, wherein the DNA backbone is a DNA vector selected from a group consisting of plasmid, phagemid, cosmid, and fosmid.

38. The method according to claim 1, wherein the DNA backbone contains one or more sequences that are capable of mediating bacteria phage packaging.

39. The method according to claim 38, wherein the bacteria phage packaging sequence is the COS sequence derived from bacteria phage lambda.

40. The method according to claim 1, wherein the DNA backbone comprises a selection marker gene.

41. The method according to claim 1, wherein the structural information of interest of the GVT-pair on the subject nucleic acid molecule is separation distance between the GVT-pair on the subject nucleic acid molecule;
   wherein the corresponding structural information of interest of the segments on the reference nucleic acid molecule is separation distance between the segments on the reference nucleic acid molecule; and
   wherein the fine-structural-variation of the subject nucleic acid molecule is determined by comparing the separation distance between the GVT-pair with the separation distance between the segments on the reference nucleic acid molecule.

42. The method according to claim 1, wherein the structural information of interest of the GVT-pair on the subject nucleic acid molecule is orientation between the GVT-pair on the subject nucleic acid molecule;
   wherein the corresponding structural information of interest of the segments on the reference nucleic acid molecule is orientation between the segments on the reference nucleic acid molecule; and
   wherein the fine-structural-variation of the subject nucleic acid molecule is determined by comparing the orientation between the GVT-pair with the orientation between the segments on the reference nucleic acid molecule.

* * * * *

UNITED STATES PATENT AND TRADEMARK OFFICE
CERTIFICATE OF CORRECTION

PATENT NO. : 8,329,400 B2  
APPLICATION NO. : 12/501136  
DATED : December 11, 2012  
INVENTOR(S) : Si Lok Page 1 of 1

It is certified that error appears in the above-identified patent and that said Letters Patent is hereby corrected as shown below:

Column 3,  
Line 62, "a type ITS or" should read --a type IIS or--.

Column 4,  
Line 43, "type ITS restriction" should read --type IIS restriction--.

Column 9,  
Line 23, "separation of 5-kb" should read --separation of ~5-kb--.

Column 18,  
Line 53, "of 20,000 to 50,000" should read --of ~20,000 to 50,000--.

Column 22,  
Lines 4-5, "density of 20,000 to 50,000" should read --density of ~20,000 to 50,000--.

Column 28,  
Line 35, "produced firm" should read --produced from--.

Column 33,  
Line 28, "Modem molecular" should read --Modern molecular--.  
Line 65, "43204321" should read --4320-4321--.

Signed and Sealed this  
Twelfth Day of March, 2013

Teresa Stanek Rea  
*Acting Director of the United States Patent and Trademark Office*